US005482957A

United States Patent [19]

[11] Patent Number: 5,482,957
[45] Date of Patent: Jan. 9, 1996

Wagner et al.

[54] AZOLE DERIVATIVES, PROCESS FOR THEIR PREPARATION AND THEIR USE

[75] Inventors: Adalbert Wagner, Hattersheim; Heinrich Englert, Hofheim am Taunus; Heinz-Werner Kleemann, Bad Homburg; Hermann Gerhards, Hofheim am Taunus; Bernward Schölkens, Kelkheim/Taunus; Reinhard Becker, Wiesbaden; Wolfgang Linz, Mainz, all of Germany; Jean-Paul Vevert, Pantin; John-Claude Caille, Angers, both of France

[73] Assignee: Hoechst Aktiengesellschaft, Frankfurt am Main, Germany

[21] Appl. No.: 234,591

[22] Filed: Apr. 28, 1994

Related U.S. Application Data

[63] Continuation of Ser. No. 806,634, Dec. 13, 1991, abandoned.

[30] Foreign Application Priority Data

| | | | |
|---|---|---|---|
| Jan. 4, 1991 | [DE] | Germany | 41 00 109.5 |
| Mar. 26, 1991 | [DE] | Germany | 41 09 949.4 |
| Jun. 27, 1991 | [DE] | Germany | 41 21 229.0 |

[51] Int. Cl.[6] ........ A61K 31/41; C07D 233/66

[52] U.S. Cl. ........ 514/398; 514/381; 514/397; 514/400; 514/227.8; 514/235.8; 514/275; 514/316; 514/326; 514/341; 544/58.4; 544/139; 544/331; 546/278; 546/210; 546/187; 548/196; 548/251; 548/312.4; 548/315.1; 548/315.4; 548/322.5; 548/334.5; 548/342.5; 548/313.7

[58] Field of Search ........ 548/251, 342.5, 548/196, 315.4, 312.4, 313.7, 334.5, 322.5, 315.1; 546/278, 210, 187; 544/331, 139, 58.4; 514/400, 381, 371, 397, 341, 326, 316, 275, 235.8, 227.8, 398

[56] References Cited

U.S. PATENT DOCUMENTS

| | | | |
|---|---|---|---|
| 4,355,044 | 10/1982 | Heller | 424/319 |
| 5,064,825 | 11/1991 | Chakravarty et al. | 514/221 |
| 5,087,634 | 2/1992 | Reitz et al. | 548/323.5 |
| 5,126,342 | 6/1992 | Chakravarty et al. | 514/235.8 |
| 5,128,355 | 7/1992 | Carini et al. | 514/381 |
| 5,138,069 | 8/1992 | Carini et al. | 548/253 |
| 5,155,118 | 10/1992 | Carini et al. | 514/381 |
| 5,236,928 | 8/1993 | Chakravarty et al. | 548/323.5 |

FOREIGN PATENT DOCUMENTS

| | | | |
|---|---|---|---|
| 0503162A1 | 9/1962 | European Pat. Off. . | |
| 0028834 | 5/1981 | European Pat. Off. | 548/250 |
| 0324377 | 7/1987 | European Pat. Off. | 548/250 |
| 0253310 | 1/1988 | European Pat. Off. | 548/250 |
| 0323841 | 7/1989 | European Pat. Off. | 548/250 |
| 0401030 | 12/1990 | European Pat. Off. | 548/250 |
| 0409332 | 1/1991 | European Pat. Off. | 548/250 |
| 4010797 | 10/1991 | Germany | 548/250 |

OTHER PUBLICATIONS

Remington's Pharmaceutical Sciences, 17th Edition, Chapter 76, pp. 1418–1419, 1968.

Dr. J. Mathieu et al., "Nucleofuger und elektrofuger Austritt," Angew. Chem., vol. 72, pp. 71–74 (1960).

CA 115:29326q, Substituted imidazo- . . . antagonists Chakravarty et al. p. 778, 1991.

*Primary Examiner*—Joseph K. McKane
*Attorney, Agent, or Firm*—Finnegan, Henderson, Farabow, Garrett & Dunner

[57] ABSTRACT

Azole derivatives, process for their preparation, and their use

Azole derivatives of the formula (I)

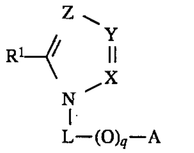

(I)

in which A, L, O, $R^1$, X, Y, Z and q have the meanings given, process for their preparation, pharmaceutical preparations and the use of the compounds are described. Azole derivatives of the formula I where the symbols have for example the following meanings:

$R^1$ is $(C_2-C_{10})$-alkyl,

Z is nitrogen,

X and Y are independently of one another $CR^2$,

L is $—CH_2—$, q is zero or 1,

A is a biphenyl radical which is substituted for example by $R^{15}$, $R^2$ is halogen or hydrogen, $R^{15}$ is $SO_2—NH—CO—OR^6$ and $R^6$ is phenyl, are highly active antagonists of angiotensin II receptors.

17 Claims, No Drawings

AZOLE DERIVATIVES, PROCESS FOR THEIR PREPARATION AND THEIR USE

This application is a continuation of prior application Ser. No. 07/806,634 filed Dec. 13, 1991, now abandoned.

Growing importance is attached to the development of novel angiotensin II receptor antagonists. 1-Benzyl-substituted imidazole derivatives are known from EP-A-28,834, imidazole derivatives having a diarylcarboxylic function are known from EP-A-253,310 and EP-A-0,401,030, pyrazole and triazole derivatives are known from EP-A-323,841 and triazole derivatives in each case having a diarylcarboxylic function are known from EP-A-0,409,332, and imidazole derivatives having a diaryltetrazolyl group and their use as antagonists of angiotensin II receptors are known from EP-A-324,377.

Moreover, substituted azoles which contain a sulfonylurea group are presented in DE-A-4,010,797 (corresponding to U.S. patent application No. 07/679.233).

Novel azole derivatives have been found which have a novel sulfonylurea, sulfonylurethane or a sulfonylsulfonamide structure and which are highly active antagonists of angiotensin II receptors both in vitro and in vivo.

The invention relates to compounds of the formula I

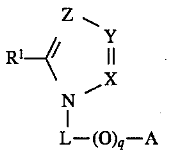

(I)

in which the symbols have the following meanings:

a) X, Y and Z are identical or different and are N or $CR^2$, b) $R^1$ is

1. $(C_2-C_{10})$-alkyl,
2. $(C_3-C_{10})$-alkenyl,
3. $(C_3-C_{10})$-alkynyl,
4. $-OR^3$,
5. $(C_3-C_8)$-cycloalkyl,
6. $(C_4-C_{10})$-cycloalkylalkyl,
7. $(C_5-C_{10})$-cycloalkylalkenyl,
8. $(C_5-C_{10})$-cycloalkylalkynyl,
9. $-(CH_2)_m-B-(CH_2)_n-R^4$,
10. -benzyl,
11. a radical as defined under b) 1., 2., 3. or 9 , which is monosubstituted by $CO_2R^3$,
12. a radical defined as under b) 1., 2., 3. or 9., in which 1 to all of the hydrogen atoms are substituted by fluorine, or
13. the radical defined under b) 10., which is substituted on the phenyl by 1 or 2 identical or different radicals from the series comprising halogen, $(C_1-C_4)$-alkoxy and nitro;

c) $R^2$ is 1. hydrogen,
2. halogen,
3. nitro,
4. $C_vF_{2v+1}$,
5. pentafluorophenyl,
6. cyano,
7. $-O-R^6$,
8. phenyl,
9. phenyl-$(C_1-C_3)$-alkyl, 10. $(C_1-C_{10})$-alkyl,
11. $(C_3-C_{10})$-alkenyl,
12. phenyl-$(C_2-C_6)$-alkenyl,
13. 1-imidazolyl-$(CH_2)_m$—,
14. 1,2,3-triazolyl-$(CH_2)_n$—,
15. tetrazolyl-$(CH_2)_m$—,
16. $-(CH_2)_{o-1}-CHR^7-OR^5$,
17. $-(CH_2)_o-O-CO-R^3$,
18. $-(CH_2)_o-S-R^6$,
19. $-S(O)_r-R^{19}$,
20. $-CH=CH-(CH_2)_m-CHR^3-OR^6$,
21. $-CH_2=CH-(CH_2)_m-CO-R^8$,
22. $-CO-R^8$,
23. $-CH=CH-(CH_2)_m-O-CO-R^7$,
24. $-(CH_2)_m-CH(CH_3)-CO-R^8$,
25. $-(CH_2)_o-CO-R^8$, 26. 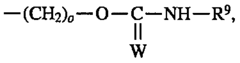

27. 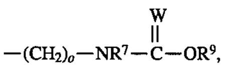

28. $-(CH_2)_o-NR^7-CO-NHR^9$,
29. $-(CH_2)_o-NR^7-SO_2R^9$,

30. 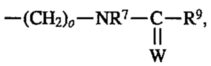

31. $-(CH_2)_nF$,
32. $-(CH_2)_n-O-NO_2$,
33. $-(CH_2-N_3$,
34. $-(CH_2)_n-NO_2$,
35. $-CH=N-NR^5R^7$,
36. phthalaimido-$(CH_2)_n$—, 37. 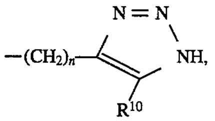

38. 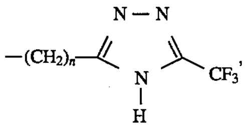

39. 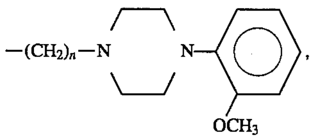

40. 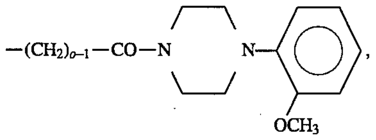

42. 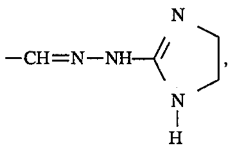,

43. $-(CH_2)_n-SO_2-NR^7-CS-NR^6R^9$,

44. $-(CH_2)_n-SO_2-NR^7-CO-NR^6R^9$,

45. $-(CH_2)_o-SO_2R^9$, 46. a radical defined as under c) 8. or 9., which is substituted on the phenyl by 1 or 2 identical or different radicals from the series comprising halogen, hydroxyl, methoxy, trifluoromethyl, $CO_2R^3$ and phenyl, 47. a radical defined as under c) 10., 11. or 19., in which one to all of the hydrogen atoms are substituted by fluorine, or 48. the radical defined under c) 14., which is substituted by 1 or 2 identical or different radicals from the series comprising methoxycarbonyl and $(C_1-C_4)$-alkyl, 49. $-(CH_2)_n-SO_2-NR^7-CO-R^6$, 50. $-(CH_2)_n-SO_2-NR^7-CS-R^6$;

d) R3 is 1. hydrogen,
2. $(C_1-C_8)$-alkyl,
3. $(C_3-C_8)$-cycloalkyl,
4. phenyl,
5. benzyl or
6. the radical defined under d) 2., in which 1 to all of the hydrogen atoms are substituted by fluorine;

e) $R^4$ is 1. hydrogen,
2. $(C_1-C_6)$-alkyl,
3. $(C_3-C_8)$-cycloalkyl,
4. $(C_2-C_4)$-alkenyl or
5. $(C_2-C_4)$-alkynyl;

f) $R^5$ is 1. hydrogen,
2. $(C_1-C_6)$-alkyl,
3. $(C_3-C_8)$-cycloalkyl,
4. phenyl or
5. benzyl;

g) $R^6$ and $R^9$ are identical or different and are 1. hydrogen
2. $(C_1-C_6)$-alkyl which can be substituted by 1-3 radicals from the series comprising $(C_1-C_6)$-alkoxy, which for its part can be substituted by 1-3 radicals from the series comprising hydroxyl, $(C_1-C_6)$-alkoxy, amino, mono-$(C_1-C_6)$-alkylamino and di-$(C_1-C_6)$-alkylamino, or can be substituted by $(C_2-C_{10})$-alkenyl, hydroxyl, amino, mono-$(C_1-C_6)$-alkylamino, di-$(C_1-C_6)$-alkylamino, $(C_1-C_6)$-alkoxycarbonylamino, $(C_6-C_{12})$-aryl-$(C_1-C_4)$-alkoxycarbonylamino, $(C_6-C_{10})$-aryl, $(C_6-C_{10})$-aryl(C-$C_3$)-alkyl, $(C_1-C_9)$-heteroaryl, carboxyl and $(C_1-C_4)$-alkoxycarbonyl,
3. $(C_3-C_8)$-cycloalkyl, where the cycloalkyl moiety can additionally be substituted by 1-3 radicals from the series comprising $(C_1-C_4)$-alkyl and $(C_2-C_4)$-alkenyl,
4. $(C_3-C_8)$-cycloalkyl-$(C_1-C_3)$-alkyl,
5. $(C_6-C_{12})$-aryl, preferably phenyl, 6. $(C_6-C_{10})$-aryl-$(C_1-C_4)$-alkyl,
7. $(C_1-C_9)$-heteroaryl which can be partially or completely hydrogenated,
8. a radical defined as under g) 5., 6., 7., 9., 15., 16., 17., 19., 20. or 21., substituted by 1 or 2 identical or different radicals from the series comprising halogen, hydroxyl, $(C_1-C_4)$-alkyl, methoxy, nitro, cyano, $CO_2R^3$, trifluoromethyl, $-NR^{11}R^{12}$ and

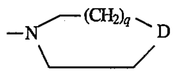

9. $(C_1-C_9)$-heteroaryl-$(C_1-C_3)$-alkyl, where the heteroaryl moiety can be partially or completely hydrogenated,
10. $(C_1-C_6)$-alkyl in which 1 to all hydrogen atoms are substituted by fluorine,
11. $(C_2-C_{10})$-alkenyl, $(C_2-C_{10})$-alkenoyl or $(C_2-C_{10})$-alkadienyl,
12. $(C_3-C_8)$-cycloalkenyl,
13. $(C_3-C_8)$-cycloalkenyl-$(C_1-C_3)$-alkyl,
14. bi- or tricyclic $(C_4-C_{10})$-cycloalkenyl-$(C_1-C_4)$-alkyl which can additionally be substituted by 1-3 $(C_1-C_4)$-alkyl radicals,
15. $(C_6-C_{10})$-aryl-$(C_1-C_4)$-alkyl,
16. $(C_6-C_{10})$-aryl-$(C_3-C_6)$-alkenyl,
17. $(C_1-C_9)$-hetaryl-$(C_3-C_6)$-alkenyl,
18. $(C_3-C_6)$-alkynyl,
19. $(C_6-C_{10})$-aryl-$(C_3-C_6)$-alkynyl,
20. $(C_1-C_9)$-hetaryl-$(C_3-C_6)$-alkynyl,
21. $R^6$ and $R^9$, together with the N atom carrying them, are a hetaryl, which can also be partially or completely hydrogenated;

h) $R^7$ is 1. hydrogen,
2. $(C_1-C_6)$-alkyl,
3. $(C_3-C_8)$-cycloalkyl,
4. $(C_6-C_{12})$-aryl-$(C_1-C_6)$-alkyl, preferably benzyl,
5. phenyl or
6. $(C_1-C_9)$-heteroaryl;

i) $R^8$ is 1. hydrogen,
2. $(C_1-C_6)$-alkyl,
3. $(C_3-C_8)$-cycloalkyl,
4. phenyl-$(CH_2)_q$—,
5. $OR^6$,
6. $NR^{11}R^{12}$ or
7. 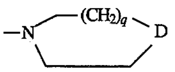

j) $R^{10}$ is cyano, nitro or $CO_2R^7$;

k) $R^{11}$ and $R^{12}$ are identical or different and are 1. hydrogen,
2. $(C_1-C_4)$-alkyl,
3. phenyl,
4. benzyl or
5. α-methylbenzyl;

l) D is $NR^{13}$, O or $CH_2$;

m) $R^{13}$ is hydrogen, $(C_1-C_4)$-alkyl or phenyl;

n) A is a biphenyl radical which can be substituted by up to 4, preferably up to 2, identical or different radicals $R^{14}$ or $R^{15}$, where A, however, is compulsorily substituted by at least one radical defined under p) 44. or 45.

o) $R^{14}$ is 1. halogen,
2. nitroso,
3. nitro,
4. amino,
5. cyano,
6. hydroxyl,
7. $(C_1-C_6)$-alkyl,
8. $(C_1-C_4)$-alkanoyl,
9. $(C_1-C_4)$-alkanoyloxy,
10. $CO_2R^3$,
11. methanesulfonylamino,
12. trifluoromethanesulfonylamino,
13. $—CO—NH—OR^9$,
14. $—SO_2—NR^6R^7$,
15. $—CH_2—OR^7$,
16. $(C_1-C_9)$-heteroaryl-$(CH_2)_q$—, preferably 1-tetrazolyl,
17. $(C_7-C_{13})$-aroyl, 18. 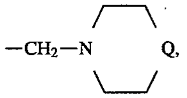

19. 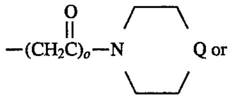 or

20. $(C_6-C_{12})$-aryl;

p) $R^{15}$ is 1. hydrogen,
2. $(C_1-C_6)$-alkyl,
3. $(C_3-C_8)$-cycloalkyl,
4. $(C_8-C_{12})$-aryl,
5. $(C_7-C_{13})$-aroyl,
6. $(C_1-C_4)$-alkoxy,
7. $(C_1-C_4)$-alkanoyloxy,
8. $(C_1-C_9)$-heteroaryl,
9. $CO_2R^3$,
10. halogen,
11. cyano,
12. nitro,
13. $NR^6R^7$,
14. hydroxyl,
15. $—CO—NH—CHR^5—CO_2R^3$,
16. sulfo,
17. $—SO_3R^3$,
18. $—SO_2—NR^7—CO—NR^6R^9$ or $—SO_2—NR^7—CS—NR^6R^9$,
19. $—NR^7—CO—NR^7SO_2—CH_2—R^5$,
20. $—C(CF_3)_2OH$,
21. phosphonooxy,
22. $—PO_3H_2$, 23. $—NH—PO(OH)_2$,
24. $—S(O)_rR^6$,
25. $—CO—R^8$,
26. $—CO—NR^6R^9$,
27. $—CR^{20}(OH)—PO(OH)_2$,
28. the radical defined under o) 20.

29. 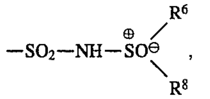

30. 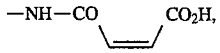

31. 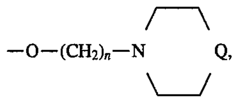

32. 5-tetrazolyl—NH—CO—,
33. $—CO—NH—NH—SO_2CF_3$,

34. 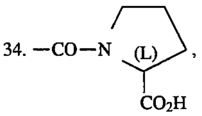

35. 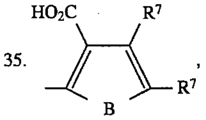

36. 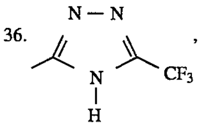

37. 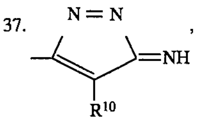

38. 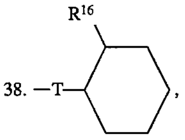

39. 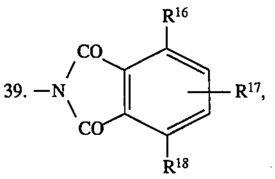

40. $—CO—NH—SO_2—R^{19}$,
41. $—SO_2—NH—CO—R^6$ or
42. the radical defined under p) 4., substituted by 1 or 2 identical or different radicals from the series comprising halogen, cyano, nitro, NR6$R^7$ and hydroxyl;
43. $R^{15}$ together with $R^{14}$ is $—CO—NH—SO_2—$,
44. $—SO_2—NH—CO—O—R^6$
45. $—SO_2—NH—SO_2—NR^6R^9$

46. $—SO_2—NH—SO_2—R^6$ q) B is O, $NR^7$ or S;

r) W is O or S;

s) L is $(C_1–C_3)$-alkanediyl;

t) $R^{16}$ is $CO_2R^3$ or $CH_2CO_2R^3$;

u) $R^{17}$ is hydrogen, halogen, $(C_1–C_4)$-alkyl or $(C_1–C_4)$-alkoxy;

v) $R^{18}$ is hydrogen, $(C_1–C_4)$-alkyl or phenyl;

w) $R^{19}$ is

1. $(C_1–C_6)$-alkyl,
2. $(C_3–C_8)$-cycloalkyl,
3. phenyl,
4. benzyl or
5. the radical defined under w) 1., in which one to all of the hydrogen atoms are substituted by fluorine;

x) T is 1. a single bond,
2. —CO—,
3. $—CH_2—$,
4. —O—,
5. —S—,
6. $—NR^{21}—$,
7. $—CO—NR^{21}—$,
8. $—NR^{21}—CO—$,
9. $—O—CH_2—$,
10. $—CH_2—O—$,
11. $—S—CH_2—$,
12. $—CH_2—S—$,
13. $—NH—CR_{20}R^{22}—$,
14. $—NR^{21}—SO_2—$,
15. $SO_2—NR^{21}—$,
16. $—CR_{20}R^{22}—NH—$,
17. —CH=CH—,
18. —CF=CF—,
19. —CH=CF—,
20. —CF=CH—,
21. $—CH_2—CH_2—$,
22. $—CF_2—CF_2—$,
23. $—CH(OR^3)—$
24. $—CH(OCOR^5)—$ 25. 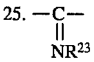 or 26. 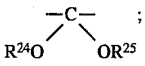 ;

y) $R^{20}$ and $R^{22}$ are identical or different and are hydrogen, $(C_1–C_5)$-alkyl, phenyl, allyl or benzyl;

z) $R^{21}$ is hydrogen, $(C_1–C_6)$-alkyl, benzyl or allyl;

a') $R^{23}$ is

1. $NR^{20}R^{21}$,
2. ureido,
3. thioureido,
4. toluene-4-sulfonyl or
5. benzenesulfonylamino;

b') $R^{24}$ and $R^{25}$ are identical or different and are $(C_1–C_4)$-alkyl or together are $—(CH_2)_q—$;

c') Q is $CH_2$, NH, O or S;

d') m is an integer from O to 5;

e') n is an integer from 1 to 5;

f') o is an integer from 1 to 10;

g') q is 0 or 1;

h') r is 0, 1 or 2, or i') v is an integer from 1 to 6;

and their physiologically tolerable salts with the exception of the compound of the formula α

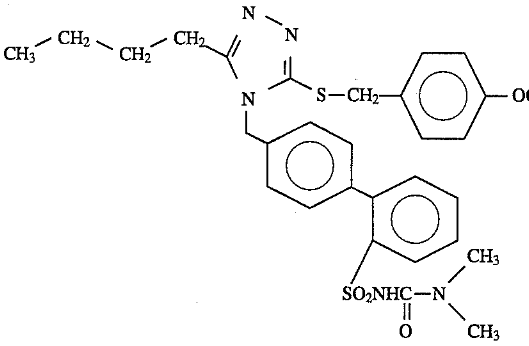

α

Alkyl, alkenyl and alkynyl can be straight-chain or branched. The same applies to radicals derived therefrom, such as alkanoyl or alkoxy.

Cycloalkyl is also understood as meaning alkyl-substituted rings.

$(C_6–C_{12})$-aryl is, for example, phenyl, naphthyl or biphenylyl, preferably phenyl. The same applies to radicals derived therefrom, such as aroyl or aralkyl.

$(C_1–C_9)$-heteroaryl is in particular understood as meaning radicals which are derived from phenyl or naphthyl, in which one or more CH groups are replaced by nitrogen and/or in which at least two adjacent CH groups are replaced (with the formation of a five-membered aromatic ring) by S, NH or O. In addition, one or two atoms of the condensation site of bicyclic radicals (such as in indolizinyl) can also be nitrogen atoms.

Heteroaryl is in particular also furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyridazinyl, indolyl, indazolyl, quinolyl, isoquinolyl, phthalazinyl, quinoxalinyl, quinazolinyl and cinnolinyl.

Stereocenters which may occur can be of both (R) and (S) configuration.

The linkage of A takes place via an alkanediyl bridge L which is preferably a methylene group.

The methylene group is preferably directly bonded to the biphenyl radical.

Physiologically tolerable salts of compounds of the formula (I) are understood as meaning both their organic and their inorganic salts, such as are described in Remington's Pharmaceutical Sciences (17th edition, page 1418 (1985)). Owing to the physical and chemical stability and the solubility, sodium, potassium, calcium and ammonium salts, inter alia, are preferred for acid groups; salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid, inter alia, are preferred for basic groups.

Preferred compounds of the formula I are those in which a) X is N, Y is $CR^2$ and Z is $CR^2$;

b) X is $CR^2$, Y is N and Z is $CR^2$;

c) X is $CR^2$, Y is $CR^2$ and Z is N or d) X, Y and Z are in each case N.

Compounds of the formula (I) are additionally preferred in which the symbols have the following meanings:

X is N, Y is $CR_2$ and Z is $CR^2$;
X is $CR^2$, Y is N and Z is $CR^2$;
X is $CR^2$, Y is $CR^2$ and Z is N,
or
X, Y and Z are in each case N, a) $R^1$ is 1. $(C_2-C_{10})$-alkyl,
2. $(C_3-C_{10})$-alkenyl,
3. $(C_3-C_{10})$-alkynyl,
4. $(C_3-C_8)$-cycloalkyl,
5. benzyl or
6. benzyl which is substituted as described above (b 13.);

b) $R^2$ is 1. hydrogen,
2. halogen,
3. nitro,
4. $C_vF_{2v+1}$,
5. pentafluorophenyl,
6. cyano,
7. —O—$R^6$,
8. phenyl,
9. phenyl-$(C_1-C_3)$-alkyl,
10. $(C_1-C_{10})$-alkyl,
11. $(C_3-C_{10})$-alkenyl,
12. phenyl-$(C_2-C_6)$-alkenyl,
13. 1-imidazolyl-$(CH_2)_m$—,
14. 1,2,3-triazolyl-$(CH_2)_o$—,
15. tetrazolyl-$(CH_2)_m$—,
16. —$(CH_2)_{o-1}$—$CHR^7$—$OR^5$,
17. —$(CH_2)_o$—O—$COR^3$,
18. —$COR^8$,
19. —$(CH_2)_o$—CO—$R^8$,
20. $S(O)_rR^{19}$,
21. —CH=CH—$(CH_2)_m$—$CHR^3$—$OR^6$,
22. —$CH_2$=CH—$(CH_2)_m$—CO—$R^8$,
23. —$(CH_2)_o$—NH—CO—$OR^9$,
24. —$(CH_2)_o$—NH—$SO_2$—$R^9$,
25. —$(CH_2)_nF$,
26. —$(CH_2)_o$—$SO_3R^9$,
27. —$(CH_2)_n$—$SO_2$—NH—CO—$NR_6R^9$,
28. —$(CH_2)_n$—$SO_2$—NH—CS—$NR^6R^9$, or
29. a radical defined as under b) 8., 9., 10., 11. or 14., which is substituted as above under c) 46., 47. or 48. in each case as described for such a radical,
30. —$(CH_2)_n$—$SO_2$—$NR^7$—CO—$R^6$,
31. —$(CH_2)_n$—$SO_2$—$NR^7$—CS—$R^6$;

c) $R^8$ is hydrogen, $(C_1-C)$-alkyl, $OR^6$, $NR^{11}R^{12}$ or morpholino;

d) T is 1. a single bond,
2. —CO—,
3. —$CONR^{21}$—,
4. —$CH_2$—$CH_2$—,
5. —$NR^{21}$—CO—,
6. —O—$CH_2$—,
7. —$CH_2$—o—,
8. —S—$CH_{26l}$—,
9. —$CH_2$—S—, 10. —NH—$CH_2$—,
11. —$CH_2$—NH— or
12. —CH=CH— and the other radicals and variables are as defined above.

Particularly preferred compounds of the formula (I) are those in which

X is N, Y is $CR^2$ and Z is $CR^2$;
X is $CR^2$, Y is N and Z is $CR^2$;
X is $CR^2$, Y is $CR^2$ and Z is N
or
X, Y and Z are in each case N, a) $R^1$ is $(C_2-C_7)$-alkyl, $(C_3-C_7)$-alkenyl or $(C_3-C_7)$-alkynyl;

b) $R^2$ is 1. chlorine,
2. bromine,
3. $C_vF_{2v+1}$ where v=1, 2 or 3,
4. pentafluorophenyl,
5. O—$R^6$,
6. —$S(O)_rR^{19}$,
7. $(CH_2)_{o-1}$—$CHR^7$—$OR^5$,
8. $(CH_2)_o$—O—CO—$R^3$,
9. —$COR^8$,
10. —$(CH_2)_o$—CO—$R^8$,
11. —$CH_2$—NH—CO—$R^8$,
12. —$(CH_2)_o$—NH—$SO_2$—$R^9$,
13. —CH=CH—$CHR^3$—$OR^6$,
14. tetrazolyl-$(CH_2)_m$—,
15. —$(CH_2)_nSO_2$—NH—CO—$NR^6R^9$,
16. —$(CH_2)_o$—$SO_3R^9$ or $(C_1-C_6)$-alkyl which is optionally substituted by hydroxyl, preferably hydroxymethyl;

c) $R^3$ is hydrogen, $(C_1-C_4)$-alkyl or benzyl;

d) $R^6$ and $R^9$ are identical or different and are 1. hydrogen
2. $(C_1-C_6)$-alkyl which can be substituted by 1–3 radicals from the series comprising $(C_1-C_6)$-alkoxy, which for its part can be substituted by 1–3 radicals from the series comprising hydroxyl, $(C_1-C_6)$-alkoxy, amino, mono-$(C_1-C_6)$-alkylamino and di-$(C_1-C_6$-alkylamino, or can be substituted by $(C_2-C_{10})$-alkenyl, hydroxyl, amino, mono-$(C_1-C_6)$-alkylamino, di-$(C_1-C_6)$-alkylamino, $(C_1-C_6)$-alkoxycarbonylamino, $(C_6-C_{12})$-aryl-$(C_1-C_4)$-alkoxycarbonylamino, $(C_6-C_{10})$-aryl, $(C_6-C_{10})$-aryl $(C_1-C_3)$-alkyl, $(C_1-C_9)$-heteroaryl, carboxyl and $(C_1-C_4)$-alkoxycarbonyl;
3. $(C_3-C_6)$-cycloalkyl,
4. $(C_3-C_6)$-cycloalkyl-$(C_1-C_3)$-alkyl,
5. phenyl,
6. phenyl-$(C_1-C_3)$-alkyl,
7. $(C_1-C_7)$-heteroaryl which can be partially or completely hydrogenated,
8. a radical defined as under g) 5., 6., 7. or 9., 14.–16. and 18.–20., substituted by 1 or 2 identical or different radicals from the series comprising halogen, hydroxyl, $(C_1-C_4)$-alkyl, methoxy, nitro, cyano, $CO_2R^3$, trifluoromethyl, —$NR^{11}R^{12}$ and

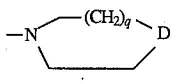

9. $(C_1-C_9)$-heteroaryl-$(C_1-C_3)$-alkyl, where the heteroaryl moiety can be partially or completely hydrogenated,
10. $(C_1-C_6)$-alkyl, in which 1 to all hydrogen atoms are substituted by fluorine,
11. $(C_2-C_4)$-alkenyl or $(C_3)$-alkenoyl,
12. $(C_3-C_6)$-cycloalkenyl,
13. $(C_3-C_6)$-cycloalkenyl-$(C_1-C_3)$-alkyl,
14. bi- or tricyclic $(C_4-C_{10})$-cycloalkenyl-$(C_1-C_4)$-alkyl which can additionally be substituted by 1–3 $(C_1-C_4)$-alkyl radicals;
15. $C_6$-aryl-$(C_1-C_3)$-alkyl,
16. $C_6$-aryl-$(C_3)$-alkenyl,
17. $(C_1-C_6)$-hetaryl-$(C_3)$-alkenyl,
18. $C_3$-alkynyl,
19. $C_3$-aryl-$(C_3)$-alkynyl,
20. $(C_1-C_6)$-hetaryl-$(C_3)$-alkynyl,
21. $R^6$ and $R^9$, together with the N atom carrying them, are a hetaryl which can also be partially or completely hydrogenated;

e) $R^7$ is hydrogen, $(C_1-C_4)$-alkyl, $(C_1-C_9)$-heteroaryl, or $(C_6-C_{12})$-aryl-$(C_1-C_4)$-alkyl;

f) $R^8$ is hydrogen, $(C_1-C_4)$-alkyl, $OR^6$ or morpholino;

g) $R^{14}$ is

1. $(C-C_4)$-alkyl,
2. $(C_1-C_4)$-alkoxy,
3. cyano,
4. amino,
5. nitroso,
6. nitro,
7. fluorine,
8. chlorine,
9. bromine,
10. $(C_1-C_9)$-heteroaryl-$CH_2$—,
11. $(C_1-C_4)$-alkanoyloxy,
12. $(C_1-C_4)$-alkanoyl,
13. benzoyl,
14. —NH—CO—$R^7$ or
15. tetrazolyl;

h) $R^{15}$ is

1. $(C_1-C_4)$-alkyl,
2. $(C_6-C_{12})$-aryl,
3. $(C_1-C_3)$-alkanoyloxy,
4. $(C_1-C_4)$-alkoxy,
5. $(C_1-C_9)$-heteroaryl, preferably 5-tetrazolyl,
6. cyano,
7. nitro,
8. hydroxyl,
9. —$S(O)_rR^6$,
10. —$SO_3R^3$,
11. chlorine,
12. bromine,
13. benzoyl,
14. —$CO_2R^3$,
15. —CO—NH—$R^6$,
16. —CO—$R^8$,
17. —$SO_2$—$NR^6R^7$,
18. —$SO_2$—NH—CO—$NR^6R^9$,
19. —$PO_3H$,
20. —CO—$CHR^5$—$CO_2H$,
21. —NH—CO—NH—$SO_2$—$CH_2$—$R^5$,
22. 5-tetrazolyl-NH—CO—,
23. 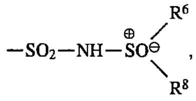 ,
24. 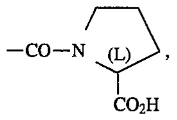 ,
25. 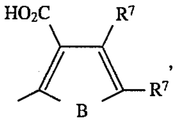 ,
26. 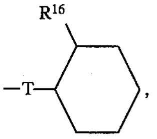 ,
27. 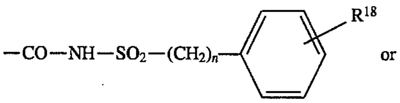 or
28. the radical defined under h) 2), substituted as defined above (see p) 42),
29. $R^{15}$ together with $R^{14}$ is —CO—NH—$SO_2$—;
30. —$SO_2$—NH—COO—$R^6$;
31. —$SO_2$—NH—$SO_2$—$NR^6R^9$;
32. —$SO_2$—NH—$SO_2$—$R^9$;

i) $R^{18}$ is hydrogen, methyl or ethyl;

j) T is a single bond, —O—, —CO—, —NHCO— or —OCH—;

k) q=0 and L is methylene and the other radicals and variables are as defined above.

Particularly preferred azole derivatives are moreover those of the general formula (I) in which Z is a nitrogen atom and Y and X are independently of one another $CR^2$ and the remaining symbols are as defined above.

Particularly suitable azole derivatives are additionally those of the general formula (I) where the symbols have the following meaning:

Z is nitrogen,

X and Y are independently of one another $CR^2$, $R^1$ is $(C_2-C_7)$-alkyl, $(C_3-C_7)$-alkenyl or $(C_3-C_7)$-alkynyl, $R^2$ is hydrogen, halogen, nitro, $(C_1-C_3)$-perfluoroalkyl, cyano, $C_1-C_{10}$)-alkyl, $(C_3-C_{10})$-alkenyl, —$CH_2OR^5$, —$S(O)_r$—$R^{19}$, —CO—$R^8$ or —O—$R^6$, $R^5$ is hydrogen or $(C_1-C_6)$-alkyl, $R^6$ and $R^9$ are 1. hydrogen,
2. $(C_1-C_6)$-alkyl which can be substituted by 1–3 radicals from the series comprising $(C_1-C_6)$-alkoxy, which for its part can be substituted by 1–3 radicals from the series comprising hydroxy, ($C_1$–$C_6$)-alkoxy, amino, mono-($C_1$–$C_6$)-alkylamino and di-($C_1$–$C_6$)-alkylamino, or can be substituted by ($C_2$–$C_{10}$)-alkenyl, hydroxyl, amino, mono-($C_1$–$C_6$)-alkylamino, di-($C_1$–$C_6$)-alkylamino, ($C_1$–$C_6$)-alkoxycarbonylamino, ($C_1$– $C_{12}$)-aryl-($C_1$–$C_4$)-alkoxycarbonylamino, ($C_6$–$C_{10}$)-aryl, ($C_6$–$C_{10}$)-aryl-($C_1$–$C_3$)-alkyl, ($C_1$–$C_9$)-heteroaryl, carboxyl and ($C_1$–$C_4$)-alkoxycarbonyl;

3. ($C_3$–$C_8$)-cycloalkyl,
4. ($C_3$–$C_6$)-cycloalkyl-($C_6$–$C_3$)-alkyl
5. ($C_6$–$C_{12}$)-aryl, preferably phenyl,
6. ($C_6$–$C_{10}$)-aryl-($C_1$–$C_4$)-alkyl,
7. ($C_1$–$C_9$)-heteroaryl, which can be partially or completely hydrogenated,
8. ($C_1$–$C_9$)-heteroaryl-($C_1$–$C_3$)-alkyl, where the heteroaryl moiety can be partially or completely hydrogenated,
9. a radical defined as above under 5., 6., 7., and 8. substituted by 1 or 2 identical or different radicals from the series comprising halogen, hydroxyl, ($C_1$–$C_4$)-alkyl, methoxy, nitro, cyano, $CO_2R^3$, trifluoromethyl, $—NR^{11}R^{12}$ and

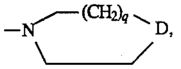

10. ($C_1$–$C_6$)-alkyl, in which 1 to all hydrogen atoms are substituted by fluorine,
11. ($C_2$–$C_6$)-alkenyl or ($C_3$–$C_6$)-alkenoyl,
12. ($C_3$–$C_8$)-cycloalkenyl,
13. ($C_6$–$C_8$)-cycloalkenyl-($C_1$–$C_3$)-alkyl,
14. ($C_6$–$C_{10}$)-aryl-($C_1$–$C_4$)-alkyl,
15. ($C_6$–$C_{10}$)-aryl-($C_3$–$C_6$)-alkenyl,
16. ($C_1$–$C_9$)-hetaryl-($C_3$–$C_6$)-alkenyl,
17. ($C_3$–$C_6$)-alkynyl,
18. ($C_6$–$C_{10}$)-aryl-($C_3$–$C_6$)-alkynyl,
19. ($C_1$–$C_9$)-hetaryl-($C_3$–$C_6$)-alkynyl,
20. $R^6$ and $R^9$, together with the N atom carrying them, are a hetaryl which can also be partially or completely hydrogenated, $R^7$ is hydrogen, $R^8$ is hydrogen or $—OR^6$, $R^{11}$ and $R^{12}$ are independently of one another hydrogen or ($C_1$–$C_4$)-alkyl, D is $—NR^{13}$, —O or $—CH_2$, $R^{13}$ is hydrogen or ($C_1$–$C_4$)-alkyl, A is a biphenyl radical which is substituted by a radical $R^{15}$ or by $R^{14}$ and $R^{15}$ together, $R^{15}$ is $—SO_2—NR^7—CO—NR^6R^9$, $—SO_2—NH—COO—R^6$, $—SO_2—NH—SO_2—NR^6R^9$, $—SO_2—NH—CO—R^6$ or $—SO_2—NH—SO_2—R^6$; or $R^{14}$ and $R^{15}$ together can be $—CO—NH—SO_2—$, L is $—CH_2—$, q is zero and r is zero, 1 or 2, and their physiologically tolerable salts.

The invention also relates to a process for the preparation of compounds of the formula (I), and of their physiologically tolerable salts, which comprises alkylating compounds of the formula (II)

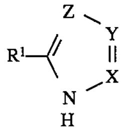
(II)

in which $R^1$, X, Y and Z are as defined above, with compounds of the formula (III)

$$U—L—(O)_q—A \qquad (III)$$

in which L, A and q are as defined above, and U is a leaving group, if appropriate removing temporarily introduced protective groups and converting sulfonamides of the formula I obtained, if appropriate, into urethanes of the formula I, converting sulfonamides of the formula I obtained or urethanes of the formula I obtained, if appropriate, into sulfonylureas of the formula I and converting the compounds of the formula (I) obtained, if appropriate, into their physiologically tolerable salts.

Suitable leaving groups U are preferably nucleofugic groups (cf. Angew. Chem. 72 [1960] 71) such as halogen, o-toluenesulfonate, mesylate or triflate.

Processes for the preparation of the precursors of the formula (II) are known, inter alia, from U.S. Pat. No. 4,355,044, EP-A-324,377 and EP-A-323,841.

Other processes are described by G. L'abbe (Chem. Rev. 69, 345 (1969)), T. Srodsky ("The Chemistry of the Azido Group", Wiley, New York, 1971, p. 331), H. Wamhoff ("Comprehensive Heterocyclic Chemistry") and by S. Katritzky Ed., Pergamon Press, New York (1984)).

Another process for the preparation of compounds of the formula II starts from 1-cyanoglyoxylic acid 2-oxime derivatives and after reduction of the oxime with reductants known from the literature and addition of mercapto compounds to the nitrile group using suitable protective groups yields precursors which can be cyclized under dehydrating conditions to give imidazoles. For the cyclization step, inter alia, mixtures of $PCl_5$ and dimethylaminopyridine (DMAP), $POCl_3$ and $SOCl_2$ and their mixtures with DMAP can be used.

The oxidation of the thio compounds of the formula I where $R^2$ is $—S(O)_rR^{19}$ and in which R is zero or 1 to the corresponding sulfones and sulfoxides is preferably carried out by means of peracids in suitable solvents such as, for example, dichloromethane.

To alkylate the azoles of the formula (II), suitable alkylating agents are, for example, appropriate benzyl halides, tosylates, mesylates or triflates or appropriate alkyl halides, tosylates, mesylates or triflates.

The alkylation is carried out in an analogous manner to processes which are known in principle.

Azole derivatives of the formula (II) are metalated, for example, in the presence of a base. Preferred bases are metal hydrides of the formula MH such as, for example, lithium hydride, sodium hydride or potassium hydride in, for example, DMF or DMSO as a solvent or metal alkoxides of the formula MOR, where R is methyl, ethyl or t-butyl, and the reaction is carried out in the corresponding alcohol, DMF or DMSO. The salts of the azoles thus formed are dissolved in an aprotic solvent such as DMF or DMSO and treated with a suitable amount of alkylating reagent.

An alternative possibility for the deprotonation of the azole derivatives is, for example, reaction with potassium carbonate in DMF or DMSO.

The reactions are carried out at temperatures below room temperature up to the boiling point of the reaction mixture, preferably between +20° C. and the boiling point of the reaction mixture, for about 1 to 10 hours.

The biphenyl derivatives can be synthesized, for example, starting from arylboronic acid derivatives by coupling with substituted aryl halides using transition metal catalysts, in particular palladium. Corresponding reactions are described by R. B. Miller et al. (Organometallics 1984, 3, 1261) or by A. Zuzuki et al. (Synthetic Commun. 11 (7), 513 (1981)).

The sulfonylurethanes of the formula I can be obtained from appropriate sulfonamides of the formula I by reaction with chlorocarbonic acid esters in inert high-boiling solvents such as, for example, toluene at temperatures of about 100° C. or the boiling points of the appropriate solvents.

Analogously, sulfonyl-sulfonamides can be prepared from the appropriate sulfonamides by reaction with sulfonyl chlorides or sulfamoyl chlorides.

The sulfonamide radical can be prepared by means of Meerwein reaction, if necessary, starting from an amino group. For this, the hydrochloride of the amine is first diazotized and then reacted with sulfur dioxide in glacial acetic acid in the presence of a copper catalyst. Subsequent action of ammonia leads to the sulfonamido group.

Alternatively, an appropriate thiophenol can be converted into a sulfonamide by oxidation with chlorine and subsequent action of ammonia.

The compounds of the formula (I) according to the invention have antagonistic action on angiotensin II receptors and can therefore be used for the treatment of angiotensin II-dependent hypertension. Possibilities of application furthermore exist in cardiac insufficiency, cardioprotection, myocardial infarct, cardiac hypertrophy, arteriosclerosis, nephropathy, kidney failure and vascular diseases of the brain such as transitory ischemic attacks and stroke.

Renin is a proteolytic enzyme of the aspartylprotease class, which is secreted into the blood circulation by the juxtaglomerular cells of the kidney as a consequence of various stimuli (volume depletion, sodium deficiency, β-receptor stimulation). In the blood, it cleaves the decapeptide angiotensin I from the angiotensinogen excreted from the liver. The former is converted into angiotensin II by the "angiotensin-converting enzyme" (ACE). Angiotensin II plays an essential role in blood pressure regulation, as it directly increases the blood pressure by means of vascular contraction. It additionally stimulates the secretion of aldosterone from the adrenal gland and in this way increases the extracellular fluid volume via the inhibition of sodium excretion, which for its part contributes to an increase in blood pressure.

Post-receptor actions are inter alia stimulation of phosphoinositol conversion ($Ca^{2+}$ release), activation of protein kinase C) and facilitation of c-E-dependent hormone receptors.

The affinity of the compounds of the formula I for the angiotensin II receptor can be determined by measurement of $^{125}$I-angiotensin II or $^{3}$H-angiotensin II displacement from receptors on membranes of the zona glomerulosa of bovine adrenal glands. For this purpose, the prepared membranes are suspended in buffer at pH 7.4.

Aprotinin, a peptidase inhibitor, is added in order to prevent the degradation of the radioligand during the incubation. About 14000 cpm of a tracer having a specific activity of 74 TBq/mmol (available from Amersham Buchler, Braunschweig, FRG) and a quantity of receptor protein which binds 50% of the tracer are additionally used. The reaction is begun by addition of 50 μl of membrane suspension to a mixture of 100 μl of buffer+aprotinin, 50 μl of buffer with or without angiotensin II or receptor antagonist and 50 μl of tracer. After an incubation time of 60 minutes at a temperature of 25° C., bound and free radioligand are separated on a Skatron® cell collector using Whatmann® GFIC filters by means of a filtration assay.

Non-specific binding is prevented by treatment of the filter with 0.3% polyethyleneimine pH=10 (Sigma, No. 3143).

The amount of displacement of the radioligand from the receptor is determined by measurement of the radioactivity in a gamma scintillation counter. The $IC_{50}$ values, which denote the concentration of inhibitor for displacing 50% of the ligand, are determined according to J. Theor. Biol. 59, 253 (1970). For the compounds of the formula (I) they are in the range from $1\times10^{-4}$–$1\times10^{-9}$M.

Alternatively, the affinity of the compounds of the formula I for the angiotensin II receptor can be determined by measurement of the $^{125}$I-angiotensin II or $^{3}$H-angiotensin II displacement of receptor preparations from various organs (liver, lung, adrenal gland, brain etc.).

To this end, the prepared membranes are suspended in an incubation buffer (20 mm Tris, pH 7.4, containing 135 mM NaCl, 10 mM KCl, 10 mM $MgCl_2$, 5 mM glucose, 0.2% bovine serum albumin and the protease inhibitors PMSF, 0.3 mM, and bacitracin, 0.1 mM) and incubated at 25° C. for 90 min together with the radioactively labeled angiotensin II and various concentrations of the compounds to be tested. Bound and free radioligand are then separated by filtration through micro glass fiber filters (GF51, Schleicher and Schüll) in a cell collector (SKATRON).

The degree of displacement of the radioligand from the receptor by the test compounds is determined by measurement of the receptor-bound radioactivity on the filters by means of a beta- or gamma-spectrometer. The amount of the displacement of the radioligand from the receptor by the test compounds is indicated by the $IC_{50}$, i.e. the concentration of the inhibitor which displaces 50% of the bound radioligand from the receptor. The calculation of the $IC_{50}$ values is carried out by means of PC software (LIGAND, G. A. McPherson 1985, Elsevier BIOSOFT, 68 Hills Road, Cambridge, CB2 1LA, UK.). The $IR_{50}$ values measured for compounds of the formula (I) are in the range from $1\times10^{-5}$ to $1\times10^{-11}$M (Table 1 which follows, in which the $IC_{50}$ values are collated for compounds according to the invention).

TABLE 1

| Example | $IC_{50}$ [nM] |
|---|---|
| 1 | 5000 |
| 2 | 8000 |
| 3 | 1100 |
| 4 | 1100 |
| 5 | 16000 |
| 22 | 2000 |
| 24 | 800 |
| 25 | 1400 |
| 29 | 1.1 |
| 30 | 2030.0 |
| 31 | 153.0 |
| 32 | 3.5 |
| 33 | 34.0 |
| 34 | 1.0 |
| 35 | 50.0 |
| 36 | 16.0 |
| 37 | 1.1 |
| 55 | 8.8 |
| 56 | 4.6 |
| 57 | 1100 |
| 58 | 3.0 |

TABLE 1-continued

| Example | $IC_{50}$ [nM] |
|---|---|
| 59 | 1.3 |
| 60 | 2.2 |
| 61 | 1.1 |
| 62 | 3.6 |
| 63 | 1.3 |
| 64 | 0.5 |
| 65 | 1.8 |
| 66 | 6.9 |
| 67 | 0.91 |
| 68 | 12.0 |
| 69 | 3.2 |
| 70 | 4.4 |
| 71 | 2.2 |
| 73 | 2.5 |
| 76 | 9.5 |
| 79 | 5.8 |
| 80 | 0.69 |
| 81 | 0.79 |
| 83 | 0.96 |
| 84 | 4.3 |
| 85 | 3.9 |
| 89 | 1.1 |
| 90 | 0.69 |
| 92 | 280.0 |
| 93 | 3.3 |
| 95 | 1.8 |
| 98 | 1.4 |
| 99 | 26.6 |
| 100 | 68.5 |
| 101 | 2.4 |
| 102 | 2.3 |
| 105 | 3.0 |
| 107 | 2.5 |
| 108 | 0.95 |
| 109 | 0.6 |
| 110 | 0.5 |
| 111 | 2.9 |
| 112 | 1.5 |
| 113 | 0.3 |
| 115 | 0.9 |
| 116 | 2.4 |
| 117 | 1.2 |
| 124 | 1.8 |
| 125 | 2.8 |
| 127 | 3.0 |
| 128 | 5.6 |
| 129 | 1.5 |
| 134 | 180.0 |
| 135 | 5.6 |
| 138 | 1.7 |
| 139 | 2.8 |
| 140 | 8.2 |
| 141 | 4.4 |
| 144 | 5.3 |
| 146 | 40.0 |
| 151 | 0.4 |
| 152 | 1.5 |
| 153 | 0.88 |
| 154 | 1.8 |
| 155 | 6.0 |
| 156 | 4.7 |
| 157 | 1.4 |
| 159 | 8.7 |
| 160 | 0.73 |
| 161 | 57.0 |
| 162 | 3.9 |
| 163 | 3.7 |
| 164 | 0.86 |
| 165 | 2.3 |
| 166 | 1.2 |
| 167 | 4.0 |
| 168 | 7.0 |
| 169 | 2.9 |
| 170 | 2.7 |
| 171 | 0.7 |
| 172 | 0.48 |
| 174 | 5.1 |

TABLE 1-continued

| Example | $IC_{50}$ [nM] |
|---|---|
| 179 | 2.6 |
| 181 | 1.0 |
| 183 | 1.7 |
| 185 | 5.9 |
| 186 | 6.5 |
| 187 | 1.2 |
| 190 | 22.0 |
| 191 | 21.4 |
| 194 | 21.7 |
| 195 | 3.0 |

To determine the antagonistic action of the compounds of the formula (I), their effect on the angiotensin II-induced blood pressure rise in anesthetized Sprague-Dawley rats can be measured. Na thiobarbital (Trapanal®, trademark of Byk Gulden, FRG) is used as an anesthetic in the dose 100 mg/kg J.p. i.v. administration is carried out in the jugular vein. The blood pressure is measured in the carotid artery. The animals are first pretreated with pentoliniumtartrate (10 mg/kg i.m.) so that a lower blood pressure level is achieved (ganglia blockade). ANG II (Hypertensin CIBA) is administered i.v. in the volume 0.1 ml/100 g at 10 minute intervals. The dose is 0.5 μg/kg. The compounds of the formula (I) are dissolved in distilled water and administered intravenously or intraduodenally in the doses 0.1 to 1.0 mg/kg, or 10 and 100 mg/kg respectively.

The compounds of the formula (I) are particularly effective in the range from 0.1–100 mg/kg, preferably 0.1–3 mg/kg.

The invention also relates to pharmaceutical compositions comprising a compound of the formula (I) and other active compounds, such as, for example, diuretics or non-steroidal anti-inflammatory active compounds. The compounds of the formula (I) can also be used as diagnostics for the renin-angiotensin system.

Pharmaceutical preparations contain an effective amount of the active compound of the formula (I) and if necessary other active compounds together with an inorganic or organic pharmaceutically utilizable excipient. Administration can be carried out intranasally, intravenously, subcutaneously or orally. The dosage of the active compound depends on the mammalian species, the body weight, the age and the manner of administration.

The pharmaceutical preparations of the present invention are prepared in a dissolving, mixing, granulating or coating process known per se.

For a form for oral administration, the active compounds are mixed with the additives customary therefor such as excipients, stabilizers or inert diluents and brought by means of customary methods into suitable administration forms such as tablets, coated tablets, hard gelatin capsules, aqueous, alcoholic or oily suspensions or aqueous, alcoholic or oily solutions. Inert excipients which can be used are, for example, gum arabic, magnesia, magnesium carbonate, potassium phosphate, lactose, glucose, magnesium stearyl fumarate or starch, in particular maize starch. The preparation in this case can be dry and moist granules. Suitable oily excipients or solvents are, for example, vegetable or animal oils, such as sunflower oil and cod liver oil.

For subcutaneous or intravenous administration, the active compounds or their physiologically tolerable salts are brought into solutions, suspensions or emulsions, if appropriate with the substances customary therefor such as solubilizers, emulsifiers or other auxiliaries. Suitable solvents are, for example, water, physiological saline solution or alcohols, such as ethanol, propanediol or glycerol, and sugar solutions such as glucose or mannitol solutions or mixtures of said solvents.

| List of abbreviations: | |
|---|---|
| DMF | N,N-dimethylformamide |
| NBS | N-bromosuccinimide |
| AIBN | α,α-azobisisobutyronitrile |
| EI | electron impact |
| DCI | desorption-chemical ionization |
| RT | room temperature |
| EA | ethyl acetate (EtOAc) |
| DIP | diisopropyl ether |
| MTB | methyl tertiary butyl ether |
| m.p. | melting point |
| HEP | n-heptane |
| DME | dimethoxyethane |
| FAB | fast atom bombardment |
| $CH_2Cl_2$ | dichloromethane |

The invention is illustrated by the following examples:

EXAMPLE 1

Synthesis of 1-[(2'-phenylaminocarbonylaminosulfonylbiphenyl- 4-yl)methyl]-2-n-butyl-4-chloroimidazole-5-carboxaldehyde

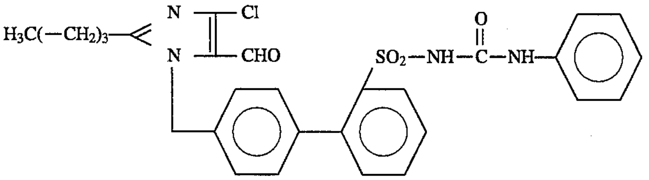

a) Preparation of 4'-methylbiphenyl-2-amine 3 g of Raney nickel are added to 23.9 g (0.112 mol) of 4'-methyl-2-nitrobiphenyl (R. B. Müller and S. Dugar, Organometallics 1984, 3, 1261) in 50 ml of methanol and the mixture is hydrogenated under normal pressure at room temperature until the theoretical amount of $H_2$ has been absorbed. The catalyst is then removed by filtration and the filtrate is concentrated. Chromatography on $SiO_2$ (500 g) using EA/HEP(1:6) as the eluent yields 19 g of the title compound as an oil (92.5%)

$R_f$(EA/HEP 1:4)=0.3 MS(EI)=183 ($M^+$)

b) 4'-Methylbiphenyl-2-ammonium hydrochloride 10 g of compound 1a) are dissolved in 50 ml of 6N HCl and 100 ml of dioxane. Removal of the solvent by distillation yields the title compound, which is used without further purification.

c) 4'-Methylbiphenyl-2-sulfonamide 7.9 g (114 mmol) of sodium nitrite are added at −10° C. to a suspension of 31 g (140 mmol) of compound 1b) in 200 ml of 6N HCl, a clear solution being formed. This is added at 0° C. to a solution containing 200 ml of glacial acetic acid, saturated with $SO_2$, 17 g of $CuCl_2.H_2O$ and 25 ml of $H_2O$. The mixture is then allowed to come to room temperature and is stirred at this temperature for 2 hours. 250 ml of EA are then added, the phases are separated and the organic phase is dried using magnesium sulfate. Concentration yields an oil, which is dissolved in 300 ml of acetone. 150 ml of 25% strength ammonia are then added and the mixture is stirred for 2 hours. It is then concentrated and 500 ml of EA are added. The EA phase is washed 1× with $H_2O$, dried using $MgSO_4$ and concentrated. Chromatography on $SiO_2$ using EA/HEP(1:1) yields the title compound (4.6 g).

$R_f$(EA/HEP 1:1)=0.25 MS(DCI)=248 ($M^++H$) M.p.: 122° C.

d) 4'-Methylbiphenyl-2-N,N-dimethylaminoformylsulfonamide 4.6 g (18.6 mmol) of compound 1c) and 2.5 g (19.3 mmol) of N,N-dimethylformamide dimethyl acetal in 30 ml of DMF are stirred at room temperature for 2 hours, then 100 ml of $H_2O$ are added and the precipitate formed is filtered off with suction and dried in the air, 4.2 g of the title compound being obtained $R_f$ (EA/HEP 1:1)=0.2 MS (DCI)=303 ($M^++H$)

e) 4'-Bromomethylbiphenyl-2-N,N-dimethylaminoformylsulfonamide 150 mg of benzoyl peroxide are added to 3.76 g (13.5 mmol) of the compound 1d) and 2.4 g of NBS (13.5 mmol) in 50 ml of chlorobenzene. After 4 hours under reflux, the mixture is concentrated, 50 ml of EA are added and the EA phase is washed once with 10% strength $Na_2SO_3$ solution and once with HaO. After drying with $Na_2SO_4$, it is concentrated and chromatographed on $SiO_2$ (eluent EA/HEP 2:1). 1.2 g of the title compound are obtained.

$R_f$ (EA/HEP 2:1)=0.23 MS (DCI)=381, 383 ($M^++H$)

f) 2-n-Butyl-4-chloro-5-formylimidazole 305 ml of a 1M $(NH_4)_2Ce(NO_3)_6$ solution in $H_2O$ are added slowly at 10°–15° C. to 20 g (0.106 mol) of 2-n-butyl-n- 4-chloro-5-hydroxymethylimidazole (prepared according to EP-A 253,310) in 350 ml of glacial acetic acid. After 2.5 h at room temperature, the pH is adjusted to 4 using 2N KOH (20° C. during the addition of the base). The mixture is then extracted 4× using 500 ml of $CH_2Cl_2$ each time and the combined organic extracts are washed 3× with 300 ml of saturated aqueous $NaHCO_3$ solution each time, dried with $Na_2SO_4$ and concentrated, the title compound being obtained as a colorless solid (18 g, 92%).

M.p.:=90° C. $R_f$ (DIP/MTB 1:1)=0.5 g) 1-[(2'-N,N-Dimethylaminoformylsulfonamidobiphenyl-4-yl)methyl]- 2-n-butyl-4-chloroimidazole-5-carboxaldehyde 690 mg (1.98mmol) of compound 1e), 370 mg (1.98 mmol) of compound 1f) and 270 mg (1.98 mmol) of potassium carbonate are stirred in DMF (10 ml) at room temperature for 2 hours. 50 ml of EA are then added and the mixture is washed twice with $H_2O$. The organic phase is dried ($Na_2SO_4$) and concentrated. Chromatography on $SiO_2$ using EA/HEP (2:1) as an eluent yields the title compound (380 mg; 40%)

$R_f$ (EA/HEP 2:1)=0.15 MS (DCI)=487 ($M^++H$)

h) 1-[(2'-Sulfonamidobiphenyl-4-yl)methyl]-2-n-butyl-4-chloroimidazole-5-carboxaldehyde 280 mg (0.58 mmol) of compound 1 g) in 7 ml of methanol and 14 ml of $H_2O$ are treated with 110 mg (2.88 mmol) of sodium hydroxide and the mixture is heated to boiling for 4 hours. After cooling to room temperature, the mixture is adjusted to approximately pH 6 using 4 N HCl and is extracted 3 times using 30 ml of EA, and the EA phases are dried ($Na_2SO_4$) and concentrated, 190 mg of the title compound being obtained.

$R_f$ (EA/HEP 2:1)=0.45 MS (DCI)=432 ($M^+$+H)

i) 1-[(2'-Phenylaminocarbonylaminosulfonylbiphenyl-4-yl)methyl]- 2-n-butyl-4-chloroimidazole-5-carboxaldehyde 730 mg (1.69 mmol) of compound 1b) are heated to 80° C. in 10 ml of phenyl isocyanate. After 4 hours, the mixture is concentrated and chromatographed on $SiO_2$ (eluent EA/HEP (251)), 400 mg of the title compound being obtained.

$R_f$ (EA/HEP 2:1)=0.15 MS (DCI)=551 ($M^+$+H)

Alternative preparation of compound 1d (4'-Methyl-2-N, N-dimethylaminoformylsulfonamide)

First 420 mg of $Pd(OAc)_2$ and then 5.66 g (41.9 mmol) of 4-tolylboronic acid in 100 ml of ethanol are added under argon to 11 g (37.9 mmol) of 2-N,N-dimethylaminoformylsulfonamidobromobenzene (prepared from 2-bromoaniline analogously to 1b–1d), 1 g of triphenylphosphine, 8 g of $Na_2CO_3$ in 150 ml of toluene and 40 ml of $H_2O$. The mixture is then heated to boiling for 4 h. It is then concentrated and taken up in 500 ml of ethyl acetate and 500 ml of $H_2O$. The resultant precipitate is filtered off and characterized as the title compound. The ethyl acetate phase is separated off, dried ($Na_2SO_4$) and concentrated. Chromatography on $SiO_2$ using ethyl acetate yields a further amount of title compound (altogether 7.6 g=66%).

Alternative preparation of 2-bromobenzenesulfonamide (to the intermediate stage analogous to 1c)

$Cl_2$ gas is introduced at 0°–10° C. for 30 min into 4.7 g of 2-bromothiophenol in 60 ml of $H_2O$. The mixture is then stirred at 0° C. for 30 min and air is subsequently blown through the solution without cooling for 30 min. After addition of 60 ml of acetone and cooling again to 0° C., 10 ml of saturated $NH_4OH$ solution are slowly added dropwise. After a further 30 min, the pH of the solution is adjusted to the value 3 using 4 n HCl and the product is obtained by filtration.

Yield 4.5 g (77%) M.p.=190°–191° C. $R_f$ (EA/H 1:1)=0.4

EXAMPLE 2

The synthesis of 1- [(2'-n-propylaminocarbonylaminosulfonylbiphenyl-4-yl)methyl]- 2-n-butyl-4-chloroimidazole-5-carboxaldehyde was carried out analogously to Example 1

$R_f$ (EA)=0.6 MS (FAB)=517 ($M^+$+H)

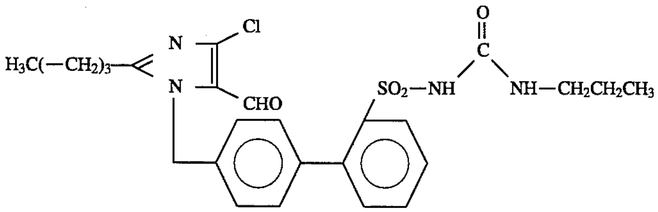

EXAMPLE 3

Synthesis of 1-[(2'-pyridyl-2-aminocarbonylaminosulfonylbiphenyl-4-yl)methyl]- 2-n-butyl-4-chloroimidazole-5-carboxaldehyde

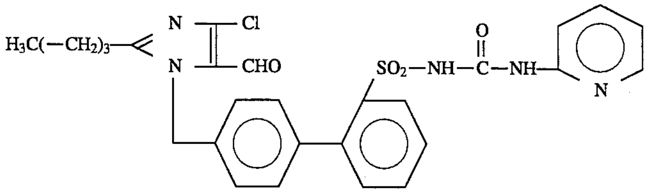

a) 1-[(2'-Ethoxycarbonylaminosulfonylbiphenyl-4-yl)methyl]- 2-n-butyl-4-chloroimidazole-5-carboxaldehyde 0.48 ml (5.1 mmol) of ethyl chloroformate is added to 1.1 g (2.5mmol) of compound 1 h) and 0.78 g (5.6 mmol) of potassium carbonate in 20 ml of dry DME. After 1 hour, the mixture is allowed to cool to room temperature and is treated with 50 ml of 10% strength $KH_2PO_4$ solution. After extraction using EA, the mixture is dried using $Na_2$ $SO_4$ and concentrated. Chromatography on $SiO_2$ using EA/HEP (2:1) as the eluent yields 840 mg of title compound.

$R_f$ (EA/HEP 2:1)=0.32 MS (DCI)=504 ($M^+$+H)

b) 1-[(2'-pyridyl-2-aminocarbonylaminosulfonylbiphenyl- 4-yl)methyl]-2-n-butyl-4-chloroimidazole-5-carboxaldehyde 150 mg (0.3 mmol) of compound 3a) and 28.5 mg (0.3 mmol) of 2-aminopyridine are heated to boiling for 2 hours in 8 ml of dry toluene. The mixture is then concentrated and chromatographed on $SiO_2$ (eluent EA), 34 mg of the title compound being obtained.

$R_f$ (EA/methanol 10:1)=0.4 MS (FAB)=552 ($M^+$+1)

The compounds of Examples 4–39 can be synthesized analogously to Example 3.

These compounds have the following formula (A)

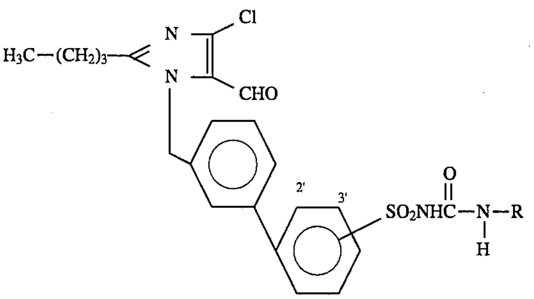
(A)
TABLE 2
| Example | MS (FAB; $M^+ + H$) | Substitution position | R |
|---|---|---|---|
| 4 (16) | 553 | 3' (2') | 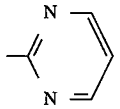 |
| 5 (17) | 543 | 3' (2') | 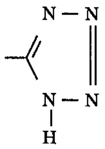 |
| 6 (18) | 558 | 3' (2') | 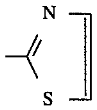 |
| 7 (19) | 559 | 3' (2') | 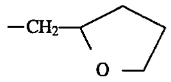 |
| 8 (20) | 597 | 3' (2') | 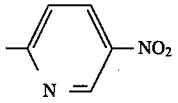 |
| 9 (21) | 541 | 3' (2') | 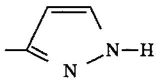 |
| 10 (22) | 596 | 3' (2') | 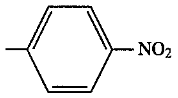 |
| 11 (23) | 596 | 3' (2') | 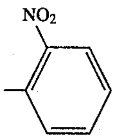 |
| 12 (24) | 569 | 3' (2') | 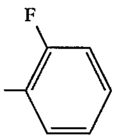 |
| 13 (25) | 569 | 3' (2') | 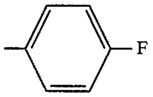 |
TABLE 2-continued
| Example | MS (FAB; $M^+ + H$) | Substitution position | R |
|---|---|---|---|
| 14 (26) | 631 | 3' (2') | 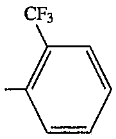 |
| 15 (27) | 631 | 3' (2') | 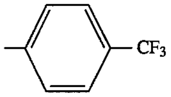 |
| 28 | 552 | 3' | 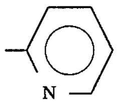 |
| 29 | 580 | 2' | 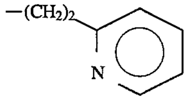 |
| 30 | 586 | 2' | 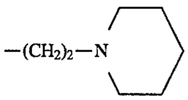 |
| 31 | 584 | 2' | 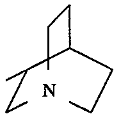 |
| 32 | 572 | 2' | 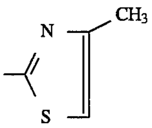 |
| 33 | 581 | 2' | 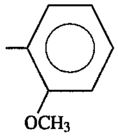 |
| 34 | 595 | 2' | 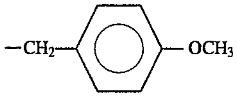 |
| 35 | 565 | 2' | 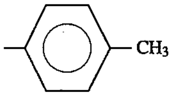 |
| 36 | 565 | 2' | 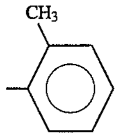 |
| 37 | 579 | 2' | 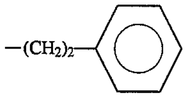 |
| 38 | 583 | 2' | 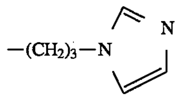 |

TABLE 2-continued

| Example | MS (FAB; $M^+ + H$) | Substitution position | R |
|---|---|---|---|
| 39 | 589 | 2' | 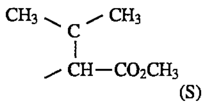 (S) |

EXAMPLE 40

Synthesis of 1-[(2'phenylaminocarbonylaminosulfonylbiphenyl-4-yl)-methyl]- 2-n-butyl-4-chloro-5-hydroxymethylimidazole 100 mg (0.18 mmol) of compound 1) are dissolved in 5 ml of ethanol and the solution is treated at room temperature with 10 mg (0.27 mmol) of sodium borohydride. After 20 hours, 20 ml of 5% strength sodium hydrogen sulfate solution are added and the mixture is extracted 3× using EA. The organic phase is dried with $Na_2SO_4$ and concentrated. Chromatography on $SiO_2$ using EA/HEP (3:1) yields 55 mg of the title compound.

$R_f$ (EA/HEP 3:1)=0.25 MS (DCI)=553 ($M^+$+H)

The compounds (see formula B) of Examples 41–54 were synthesized analogously to Example 40 from the compounds of Examples 2, 3 and 16–27 (Table 3).

TABLE 3

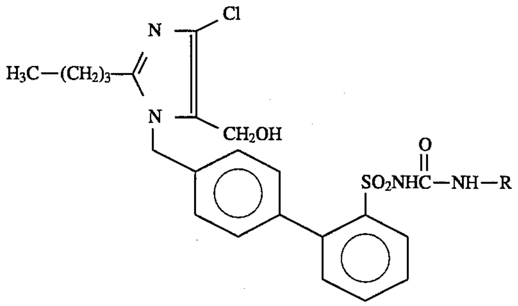

(B)

| Example | MS (FAB; $M^+ + H$) | R |
|---|---|---|
| 41 | 519 | n-propyl |
| 42 | 554 | 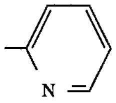 |
| 43 | 555 | 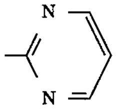 |
| 44 | 545 | 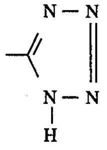 |
| 45 | 560 | 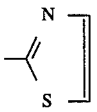 |

TABLE 3-continued

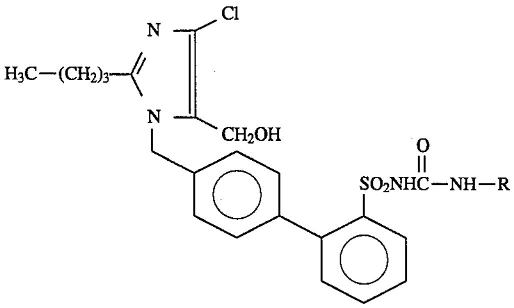

(B)

| Example | MS (FAB; $M^+ + H$) | R |
|---|---|---|
| 46 | 561 | 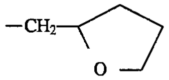 |
| 47 | 599 | 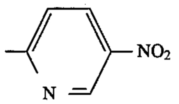 |
| 48 | 543 | 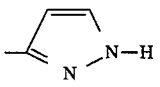 |
| 49 | 598 | 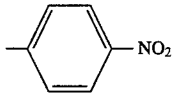 |
| 50 | 598 | 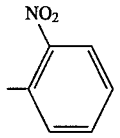 |
| 51 | 571 | 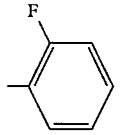 |
| 52 | 571 | 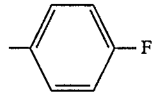 |
| 53 | 633 | 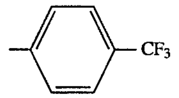 |
| 54 | 633 | 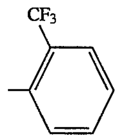 |

EXAMPLE 55

Preparation of 1-[(2'-allylaminocarbonylaminosulfonylbiphenyl- 4-yl)methyl]-2-n-butyl-4-chloroimidazole-5-carboxaldehyde

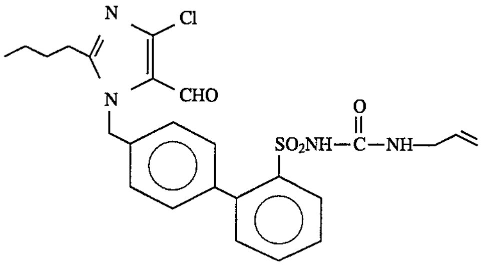

730 mg (1.69 mmol) of compound 1 h) are heated at 80° C. in 10 ml of allyl isocyanate. After 4 hours, the mixture is concentrated and chromatographed on $SiO_2$ (eluent EA/HEP (2:1)), 400 mg of the title compound being obtained.

$R_f$ (EA/HEP 2:1)=0.15 MS (FAB)-515 ($M^+$+H)

EXAMPLE 56

Preparation of 1-[(2'-allylaminocarbonylaminosulfonylbiphenyl- 4-yl)methyl]-2-n-butyl-4-methylthioimidazole-5-carboxylic acid

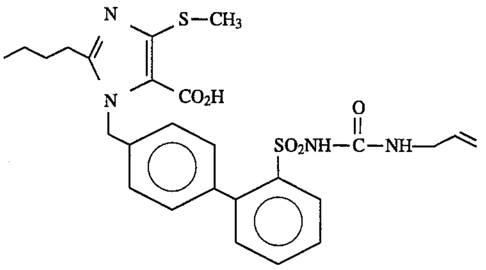

a) Ethyl 2-amino-2-cyanoacetate 119 g of sodium dithionite are added in portions (15 min) at room temperature to 35 g (0.246 mol) of ethyl 2-cyanoglyoxylate-2-oxime in 350 ml of $H_2O$ and 280 ml of saturated sodium hydrogen carbonate solution. The mixture is then warmed at 35° C. for 1 hour; it is then saturated with NaCl and extracted 5 times with dichloromethane. After drying with calcium chloride, the organic phase is concentrated. 11.8 g of the title compound are obtained as an oil.

$R_f$ ($CH_2Cl_2$/$CH_3OH$ 9:1)=0.6 b) Ethyl 2-cyano-2-n-butylcarbonylaminoacetate 3.39 ml (28.09 mmol) of valeryl chloride in 5 ml of $CH_2Cl_2$ are added dropwise at –5° C. to 0° C. to 3.6 g (28.09 mmol) of compound 56a) in 50 ml of dry $CH_2Cl_2$ and 2.3 ml (28.09 mmol) of pyridine. The mixture is then stirred at room temperature for 1 hour. The organic phase is then washed 3 times using $H_2O$ and once using saturated NaCl solution, dried using calcium chloride and concentrated. Crystallisation from DIP yields 1.7 g of the title compound.

c) Ethyl 3-amino-2-n-butylcarbonylaminomethylthioacrylate 2 ml (27.26 mmol) of condensed methylthiol are added at room temperature to 2.9 g (13.67 mmol) of compound 56b) and 0.19 ml (1.36 mmol) of triethylamine in 60 ml of absolute ethanol. After 3 days, a further 0.5 ml of methylthiol is added. After another 24 hours at room temperature, a further 0.5 ml of methylthiol and 0.19 ml of triethylamine are added by syringe and the mixture is stirred at room temperature for another 24 hours. The solvent is then removed and the residue is crystallized from DIP, 2.4 g of the title compound being obtained.

$R_f$ ($CH_2Cl_2$/EA 4:1)=0.3 M.p.: 120° C.

d) Ethyl 2-n-butyl-4-methylthioimidazole-5-carboxylate 2.44 g (20.0 mmol) of 4-dimethylaminopyridine in 12 ml of $CH_2Cl_2$ are added dropwise at –78° C. to 4.17 g (20.0 mmol) of phosphorus pentachloride in 20 ml of $CH_2Cl_2$. After 5 min, 2.42 g (10.0 mmol) of compound 56c) are added dropwise in 25 ml of $CH_2Cl_2$. The mixture is then allowed to come to room temperature and diluted with 30 ml of $CH_2Cl_2$. After 2 hours, 300 ml of 1N sodium hydrogen carbonate solution are added with ice-cooling and the mixture is stirred for 1 hour. The phases are then separated, the aqueous phase is extracted 3 times using EA and the combined organic phases are dried using calcium chloride. Chromatography on $SiO_2$ with $CH_2Cl_2$/EA (9:1)

$R_f$ ($CH_2Cl_2$/EA 9:1)=0.6 MS (DCI)=243 ($M^+$+H)

e) Ethyl 1-[(2'-sulfonamidobiphenyl-4-yl)methyl]- 2-n-butyl-4-methylthioimidazole-5-carboxylate 15 ml of conc. HCl are added to 1.35 g (2.5 mmol) of ethyl 1-[(2'-N,N-dimethylaminoformylsulfonamidobiphenyl- 4-yl)methyl]-2-n-butyl-4-methylthioimidazole-5-carboxylate [prepared from Example 56d) and Example 1e) analogously to Example 1g)] in 30 ml of methanol. After 90 min under reflux, the mixture is allowed to cool to room temperature and is adjusted to pH=5–6 using 2N NaOH solution. It is then extracted 3 times using 100 ml of EA each time, and the organic extracts are dried using $Na_2SO_4$ and concentrated, the title compound being obtained as a foam which is employed without further purification for the next reaction step.

$R_f$ (EA/HEP 1:1)=0.2 MS (FAB)=488 (M+H) f) The title compound 56 is obtained by stirring 120 mg of ethyl 1-[(2'-allylaminocarbonylaminosulfonylbiphenyl- 4-yl)methyl]-2-n-butyl-4-methylthioimidazole- 5-carboxylate (obtainable analogously to Example 55)) at room temperature for 4 days in 10 ml of ethanol and 1 ml of 2 N sodium hydroxide solution. The mixture is then concentrated, $H_2O$ is added and the mixture is adjusted to pH=4 using 1N HCl, the title compound precipitating and being isolated by filtration.

$R_f$ (EA/MeOH 10:1)=0.1 MS (FAB)=543 (M+H)

EXAMPLE 57

Synthesis of 1-[(2'-pyridylethyl-2-aminocarbonylaminosulfonylbiphenyl- 4-yl)methyl]-2-n-butyl-4-methylthioimidazol-4-carboxylic acid

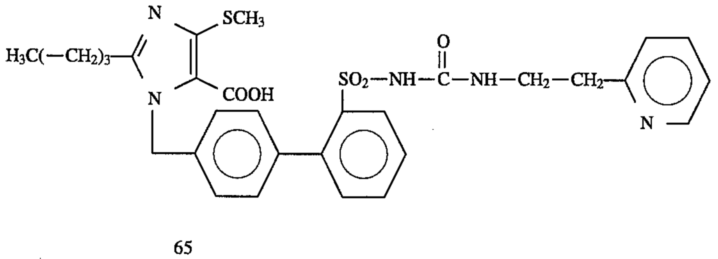

$R_f$ ($CH_2Cl_2$/$CH_3OH$ 9:1)=0.35 M.p.: 87° C.

a) Ethyl 1-[(2'-ethoxycarbonylaminosulfonylbiphenyl-4-yl)methyl]- 2-n-butyl-4-methylthioimidazole-5-carboxylate 1.21 g (2.5 mmol) of compound 56e) and 0.78 g (5.6 mmol) of potassium carbonate in 20 ml of dry DME are heated to boiling and 0.48 ml (5.1 mmol) of ethyl chloroformate is added. After 1 hour, the mixture is allowed to cool to room temperature and 50 ml of 10% strength $KH_2PO_4$ solution are added. After extraction with EA, the extract is dried using $Na_2SO_4$ and concentrated. Chromatography on $SiO_2$ using EA/HEP (2:1) as the eluent yields 840 mg of the title compound.

$R_f$ (EA/HEP 2:1)=0.5 MS (DCI)=559 ($M^+$+H)

b) Ethyl 1-[(2'-pyridylethyl-2-aminocarbonylaminosulfonylbiphenyl- 4-yl)methyl]-2-n-butyl-4-methylthioimidazole-5-carboxylate 168 mg (0.3 mmol) of compound 57a) and 37 mg (0.3 mmol) of 2-(2-aminoethyl)pyridine are heated to boiling for 2 hours in 8 ml of dry toluene. The mixture is then concentrated and chromatographed on $SiO_2$ (eluent EA), 34 mg of the title compound being obtained.

$R_f$ (EA)=0.15 MS (FAB)=636 ($M^+$+H)

c) The title compound 57 is obtained analogously to 56f) $R_f$ (EA/MeOH 5:1)=0.1 MS (FAB)=608 (M+H)

The compounds of the following Table 4 can be synthesized in a manner analogous to that in Example 57.

These compounds have the formula (C)

TABLE 4

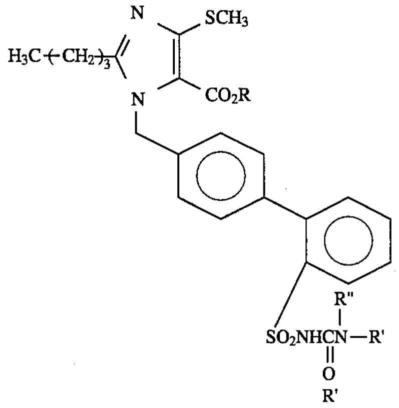

(C)

| Example | MS (FAB; $M^+$ + H) | R | R' | R" |
|---|---|---|---|---|
| 58 | 571 | $C_2H_5$ | 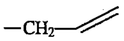 | H |
| 59 | 585 | H | 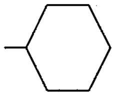 | H |
| 60 | 599 | H | 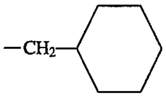 | H |
| 61 | 583 | H | 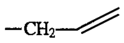 | 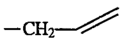 |
| 62 | 611 | H | 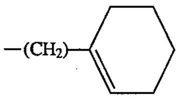 | H |
| 63 | 668 | H | 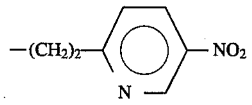 | H |
| 64 | 541 | H | $-CH_2-\equiv-H$ | H |
| 65 | 636 | $C_2H_5$ | 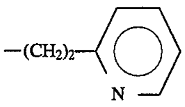 | H |
| 66 | 635 | $C_2H_5$ | 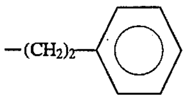 | H |

TABLE 4-continued
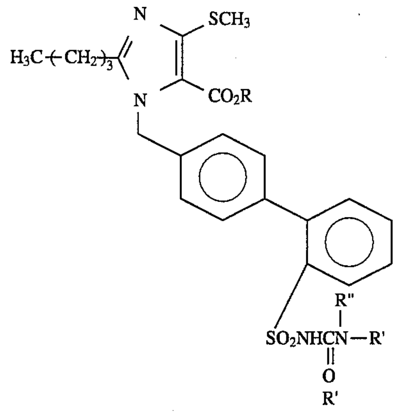
(C)
| Example | MS (FAB; $M^+ + H$) | R | R' | R" |
|---|---|---|---|---|
| 67 | 607 | H | 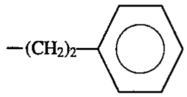 | H |
| 68 | 659 | $C_2H_5$ | 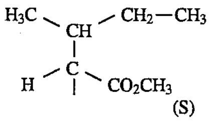 | H |
| 69 | 645 | $C_2H_5$ | 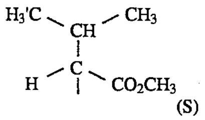 | H |
| 70 | 657 | $C_2H_5$ | 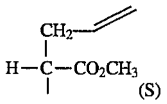 | H |
| 71 | 603 | $C_2H_5$ | $-CH_2-CO_2CH_3$ | H |
| 72 | 693 | $C_2H_5$ | 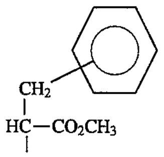 (S) | H |
| 73 | 621 | $C_2H_5$ | 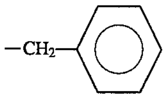 | H |
| 74 | 703 | $C_2H_5$ | 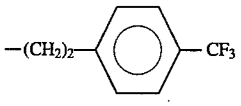 | H |
| 75 | 561 | H | 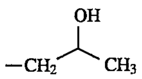 | H |
| 76 | 649 | $C_2H_5$ | 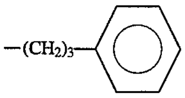 | H |

TABLE 4-continued
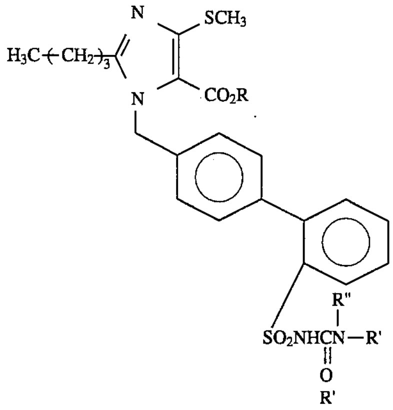
(C)
| Example | MS (FAB; $M^+ + H$) | R | R' | R" |
| --- | --- | --- | --- | --- |
| 77 | 663 | $C_2H_5$ | 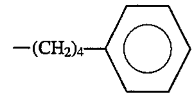 | H |
| 78 | 653 | $C_2H_5$ | 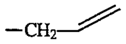 | 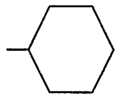 |
| 79 | 675 | H | 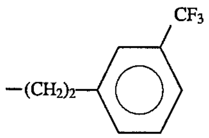 | H |
| 80 | 593 | H | 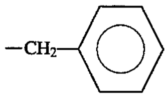 | H |
| 81 | 621 | H | 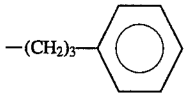 | H |
| 82 | 635 | H | 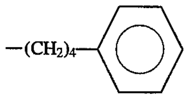 | H |
| 83 | 623 | H | 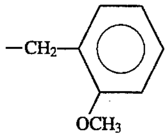 | H |
| 84 | 651 | $C_2H_5$ | 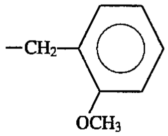 | H |
| 85 | 651 | $C_2H_5$ | 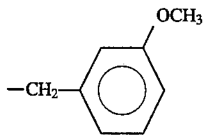 | H |

TABLE 4-continued
(C)
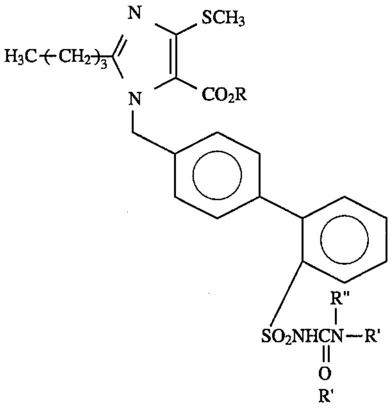
| Example | MS (FAB; $M^+ + H$) | R | R' | R" |
|---|---|---|---|---|
| 86 | 627 | $C_2H_5$ | 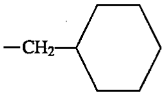 | H |
| 87 | 611 | $C_2H_5$ | 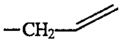 | 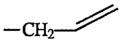 |
| 88 | 635 | $C_2H_5$ | 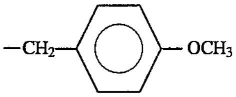 | H |
| 89 | 653 | H | 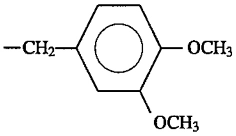 | H |
| 90 | 623 | H | 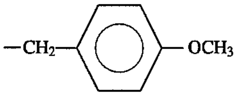 | H |
| 91 | 639 | $C_2H_5$ | 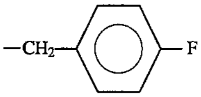 | H |
| 92 | 681 | $C_2H_5$ | 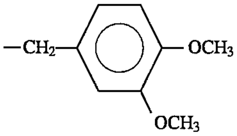 | H |
| 93 | 623 | H | 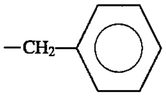 | H |
| 94 | 611 | H | 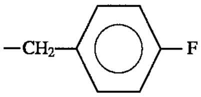 | H |
| 95 | 635 | $C_2H_5$ | 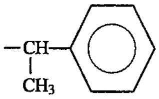 | H |

TABLE 4-continued
(C)
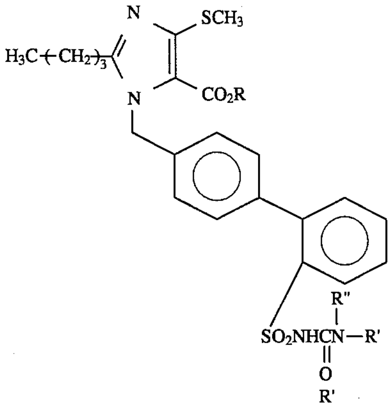
| Example | MS (FAB; M⁺ + H) | R | R' | R" |
|---|---|---|---|---|
| 96 | 625 | H | 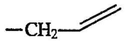 | 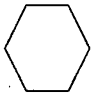 |
| 97 | 561 | H | $-CH_2-CO_2H$ | H |
| 98 | 651 | H | 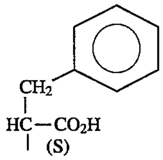 | H |
| 99 | 607 | $C_2H_5$ | 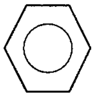 | H |
| 100 | 625 | $C_2H_5$ | 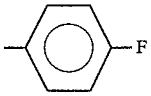 | H |
| 101 | 597 | H | 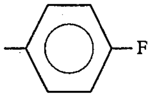 | H |
| 102 | 579 | H | 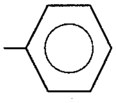 | H |
| 103 | 677 | $C_2H_5$ | 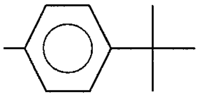 | H |
| 104 | 649 | H | 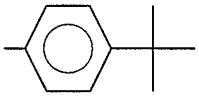 | H |
| 105 | 573 | $C_2H_5$ | $-(CH_2)_2-CH_3$ | H |
| 106 | 545 | H | $-(CH_2)_2-CH_3$ | H |
| 107 | 616 | H | 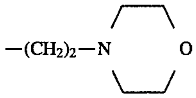 | H |

TABLE 4-continued
(C)
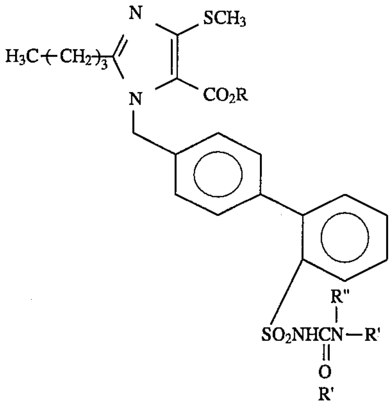
| Example | MS (FAB; M⁺ + H) | R | R' | R" |
|---|---|---|---|---|
| 108 | 614 | H | 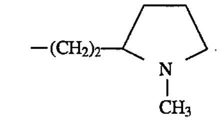 | H |
| 109 | 557 | H | 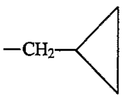 | H |
| 110 | 585 | $C_2H_5$ | 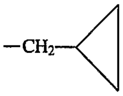 | H |
| 111 | 642 | H | 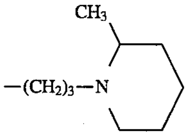 | H |
| 112 | 594 | H | 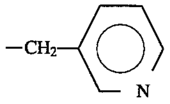 | H |
| 113 | 594 | H | 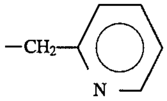 | H |
| 114 | 638 | $C_2H_5$ | 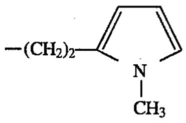 | H |
| 115 | 594 | H | 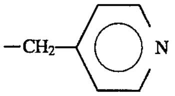 | H |
| 116 | 628 | H | 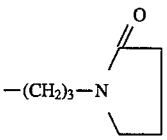 | H |

TABLE 4-continued
(C)
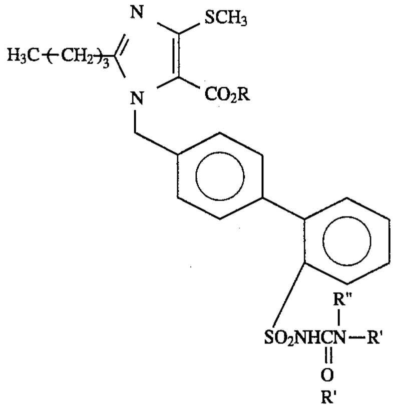
| Example | MS (FAB; $M^+ + H$) | R | R' | R" |
|---|---|---|---|---|
| 117 | 628 | $C_2H_5$ | 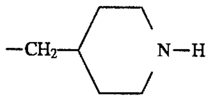 | H |
| 118 | 628 | $C_2H_5$ | 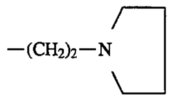 | H |
| 119 | 644 | $C_2H_5$ | 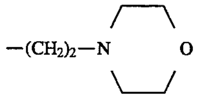 | H |
| 120 | 600 | H | 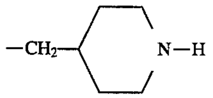 | H |
| 121 | 642 | $C_2H_5$ | 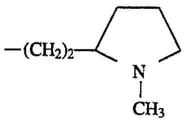 | H |
| 122 | 614 | H | 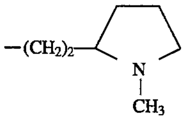 | H |
| 123 | 651 | $C_2H_5$ | 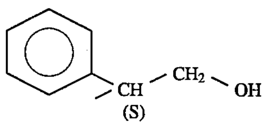 | H |
| 124 | 623 | H | 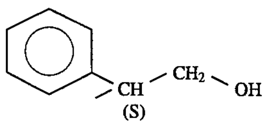 | H |
| 125 | 623 | H | 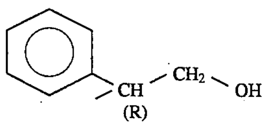 | H |

TABLE 4-continued
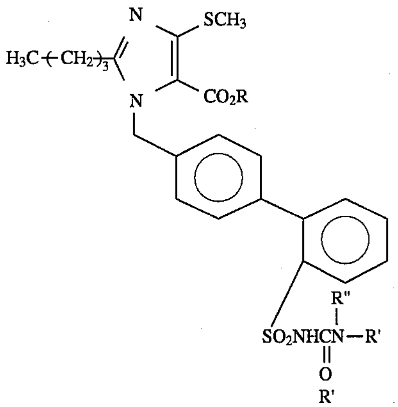
(C)
| Example | MS (FAB; $M^+ + H$) | R | R' | R" |
|---|---|---|---|---|
| 126 | 661 | $C_2H_5$ | 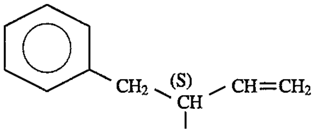 | H |
| 127 | 633 | H | 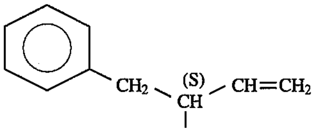 | H |
| 128 | 665 | $C_2H_5$ | 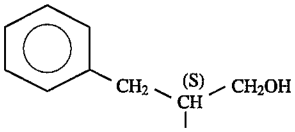 | H |
| 129 | 637 | H | 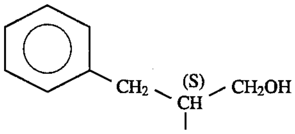 | H |
| 130 | 600 | H | 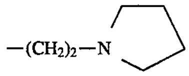 | H |
| 131 | 642 | $C_2H_5$ | 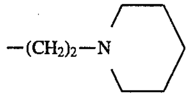 | H |
| 132 | 665 | $C_2H_5$ | 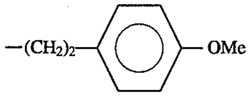 | H |
| 133 | 637 | H | 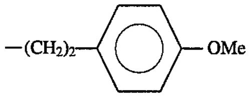 | H |
| 134 | 667 | $C_2H_5$ | 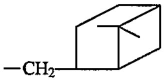 | H |

TABLE 4-continued
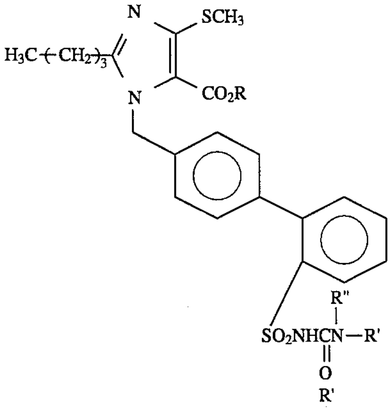
(C)
| Example | MS (FAB; $M^+ + H$) | R | R' | R" |
|---|---|---|---|---|
| 135 | 639 | H | 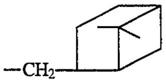 | H |
| 136 | 664 | $C_2H_5$ | 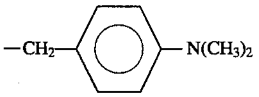 | H |
| 137 | 636 | H | 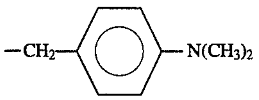 | H |
The compounds of the following Table 5 can be synthesized analogously to Example 57.
These compounds have the following formula (D)
TABLE 5
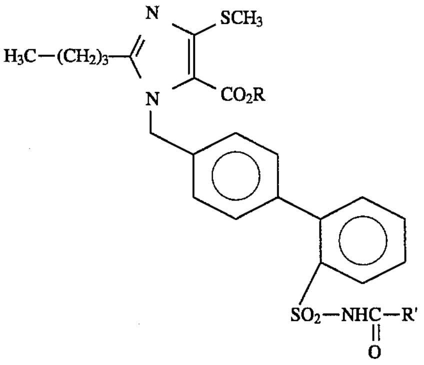
(D)
| Example | MS (FAB; $M^+ + H$) | R | R' |
|---|---|---|---|
| 138 | 581 | $C_2H_5$ | 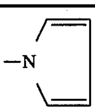 |
| 139 | 553 | H | 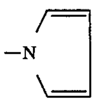 |
TABLE 5-continued
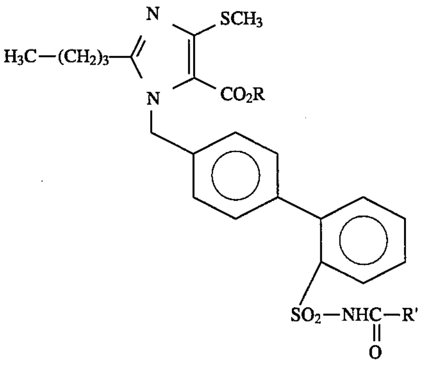
(D)
| Example | MS (FAB; $M^+ + H$) | R | R' |
|---|---|---|---|
| 140 | 601 | $C_2H_5$ | 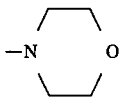 |
| 141 | 585 | $C_2H_5$ | 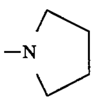 |
| 142 | 557 | H | 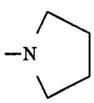 |

TABLE 5-continued

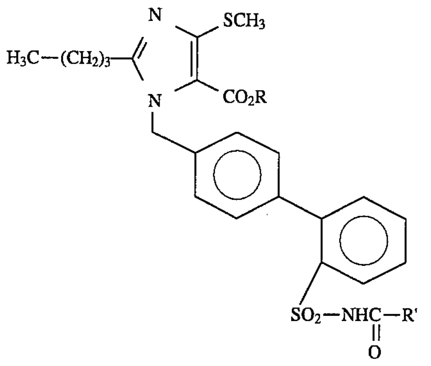

(D)

| Example | MS (FAB; $M^+ + H$) | R | R' |
|---|---|---|---|
| 143 | 573 | H | 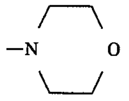 |
| 144 | 617 | $C_2H_5$ | 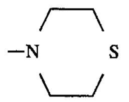 |
| 145 | 603 | $C_2H_5$ | 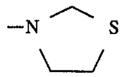 |
| 146 | 714 | $C_2H_5$ | 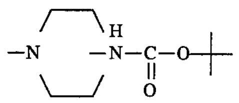 |
| 147 | 589 | H | 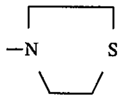 |
| 148 | 686 | H | 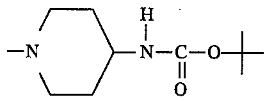 |
| 149 | 575 | H | 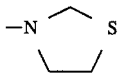 |

EXAMPLE 150

Preparation of 1-{[(2'-benzoyloxycarbonylaminosulfonyl)biphenyl- 4-yl]methyl}-2-n-butyl-4-chloroimidazol-5-carbaldehyde

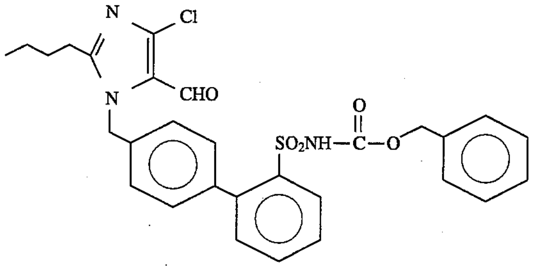

The title compound 150 is obtained by heating 215 mg (0.5 mol) of compound 1 h, 71.3 μl (0.5 mmol) of benzyl chloroformate and 70 mg (0.5 mmol) of $K_2CO_3$ in 10 ml of DMF (anhydrous) under reflux for 1.5 h. The mixture is then concentrated, 100 ml of EA are added and it is extracted once each with 40 ml of $NaHSO_4$ solution and NaCl solution. The organic phase is dried over $Na_2SO_4$ and concentrated on a rotary evaporator. Chromatography using MTB yields 120 mg (42%) of the title compound 150, m.p.=56° C.

$R_f$ (MTB)=0.20 MS (FAB)=566 ($M^+$+H)

The compounds of the following Table 6 can be synthesized analogously to Examples 150 and 57a.

These compounds have the following formula (E)

TABLE 6

(E)

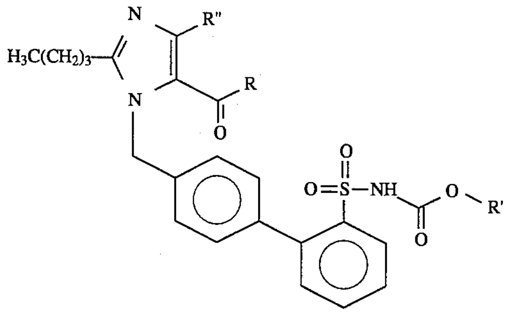

| Example | MS (FAB; $M^+ + H$) | R | R' | R" |
|---|---|---|---|---|
| 151 | 674 | $-OC_2H_5$ | $-CH_2-CH_2-Ph$ | $-SMe$ |
| 152 | 646 | $-OH$ | $-CH_2-CH_2-Ph$ | $-SMe$ |
| 153 | 558 | $-OH$ | $-CH_2-CH_2-CH=CH_2$ | $-SMe$ |
| 154 | 556 | $-OH$ | $-CH_2-CH_2-C\equiv CH$ | $-SMe$ |
| 155 | 558 | $-OH$ | 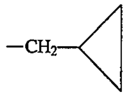 | $-SMe$ |
| 156 | 618 | $-OC_2H_5$ | $-CH_2-CH_2-O$-i-Pr | $-SMe$ |
| 157 | 590 | $-OH$ | $-CH_2-CH_2-O$-i-Pr | $-SMe$ |
| 158 | 666 | $-OC_2H_5$ | $-CH_2-CH_2-O-CH_2-Ph$ | $-SMe$ |
| 159 | 628 | $-OC_2H_5$ | 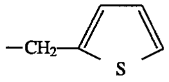 | $-SMe$ |
| 160 | 600 | $-OH$ | 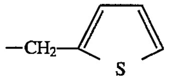 | $-SMe$ |
| 161 | 648 | $-OC_2H_5$ | $-CH_2-CH=CH-Ph$ | $-SMe$ |
| 162 | 620 | $-OH$ | $-CH_2-CH=CH-Ph$ | $-SMe$ |
| 163 | 628 | $-OC_2H_5$ | 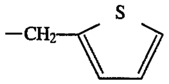 | $-SMe$ |
| 164 | 600 | $-OH$ | 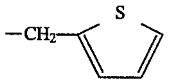 | $-SMe$ |
| 165 | 572 | $-OH$ | $-CH_2-CH=C(CH_3)_2$ | $-SMe$ |
| 166 | 558 | $-OH$ | $-CH_2-C(CH_3)=CH_2$ | $-SMe$ |
| 167 | 572 | $-OH$ | $-CH_2-CH_2-CH_2-CH=CH_2$ | $-SMe$ |
| 168 | 598 | $-OH$ | 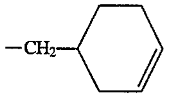 | $-SMe$ |
| 169 | 556 | $-OH$ | $-CH_2-C\equiv C-CH_3$ | $-SMe$ |
| 170 | 560 | $-OC_2H_5$ | $-CH_2-CH_3$ | $-SMe$ |
| 171 | 532 | $-OH$ | $-CH_2-CH_3$ | $-SMe$ |
| 172 | 638 | $-OH$ | $-CH_2-CH_2-O-CH_2-Ph$ | $-SMe$ |
| 173 | 600 | $-OH$ | 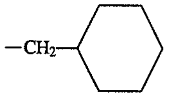 | $-SMe$ |
| 174 | 584 | $-OC_2H_5$ | $-CH_3$ | $-SMe$ |
| 175 | 556 | $-OH$ | $-CH_3$ | $-SMe$ |

TABLE 6-continued

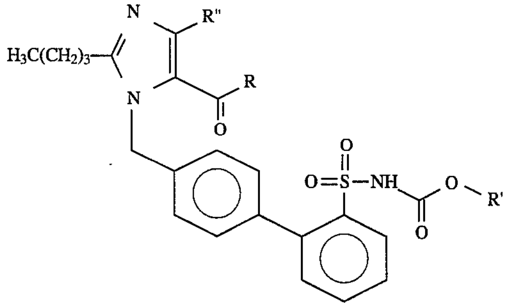

(E)

| Example | MS (FAB; $M^+ + H$) | R | R' | R'' |
|---|---|---|---|---|
| 176 | 611 | —H | 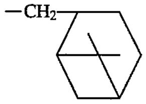 | Cl |
| 177 | 612 | —H | 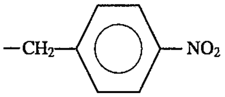 | Cl |

EXAMPLE 178

Preparation of ethyl 1-[(2'-dimethylsulfamoylaminosulfonylbiphenyl- 4-yl)methyl]-2-n-butyl-4-methylthioimidazole-5-carboxylate

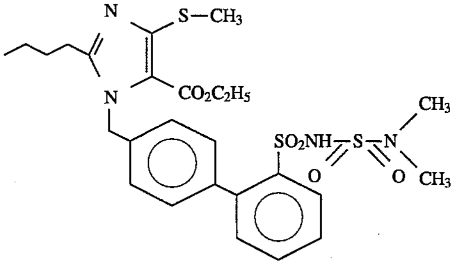

The title compound 178 is obtained by heating 244 mg (0.5 mmol) of compound 56 e), 108 μl (1.0 mmol) of sulfamoyl chloride and 140 mg (1.0 mmol) of $K_2CO_3$ in 10 ml of DME (anhydrous) to reflux for 5 days. The mixture is diluted with 50 ml of EA and washed using 50 ml of $KHSO_4/H_2SO_4$ (pH=1.0). The organic phase is dried over $Na_2SO_4$ and concentrated on a rotary evaporator. Chromatography with EA yields 69 mg (23%) of a colorless oil.

$R_f$ (EA)=0.15 MS (FAB)=617 ($M^+$+Na)

EXAMPLE 179

Preparation of 1-[1-(2'-dimethylsulfamoylaminosulfonylbiphenyl- 4-yl)methyl]-2-n-butyl-4-methylthioimidazole-5-carboxylic acid

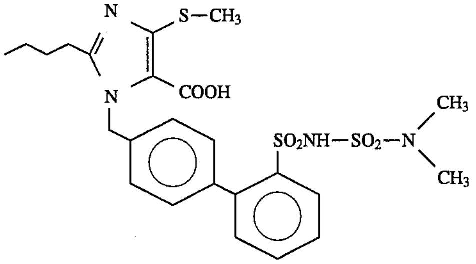

50 mg (84 μmol) of the title compound of Example 178 and 0.84 ml of 1N NaOH are dissolved in 3 ml of ethanol and stirred at RT for 2 days. The ethanol is distilled off, 5 ml of $H_2O$ are added and the mixture is adjusted to pH=2 using HCl. The precipitate is washed twice with 1 ml of water and dried in vacuo. 33 mg (70%) of a colorless powder are obtained.

$R_f$ (EA/methanol 5:1)=0.11 MS (FAB)=567 ($M^+$+H)

EXAMPLE 180

Ethyl 1-[(2'-allyloxycarbonylaminosulfonylbiphenyl-4-yl-)methyl]- 2-n-butyl-4-methylthioimidazole-5-carboxylate

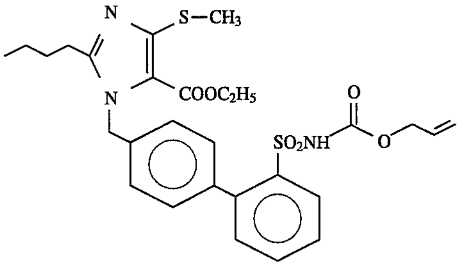

244 mg (0.5 mmol) of the compound 56 e), 106 μl (1.0 mmol) of allyl chloroformate and 140 mg (1.0 mmol) of $K_2CO_3$ are boiled under reflux for 1 h. 50 ml of 10% strength $KHSO_4$ solution are then added and the mixture is extracted 3 times using 50 ml of EA each time. The organic phase is dried over $Na_2SO_4$ and evaporated. Chromatography using MTB/DIP 1:1 yields 115 mg (40%) of a colorless oil.

$R_f$ (MTB/DIP 1:1)=0.15 MS (FAB): 572 ($M^+$+H)

EXAMPLE 181

Synthesis of 1-[(2'-allyloxycarbonylaminosulfonylbiphenyl-4-yl)methyl]- 2-n-butyl-4-methylthioimidazole-5-carboxylic acid 95 mg (0.17 mmol) of the compound 180 are hydrolyzed as described under Example 179.30 mg (33%) of a colorless foam are obtained.

$R_f$ ( EA/MeOH 10:1)=0.1 MS (FAB)=544

EXAMPLE 182

Ethyl 1-[(2'-benzyloxycarbonylaminosulfonylbiphenyl-4-yl)methyl]- 2-n-butyl-4-methylthioimidazole-5-carboxylate

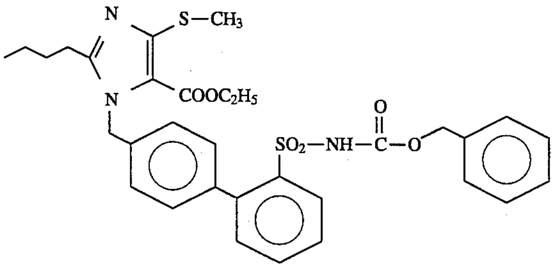

The title compound is synthesized analogously to Example 180.

$R_f$ (MTB/DIP 1:1)=0.15 MS (FAB)=622 ($M^+$+H)

EXAMPLE 183

1-[(2'-Benzyloxycarbonylaminosulfonylbiphenyl-4-yl)methyl]- 2-n-butyl-4-methylthioimidazole-5-carboxylic acid

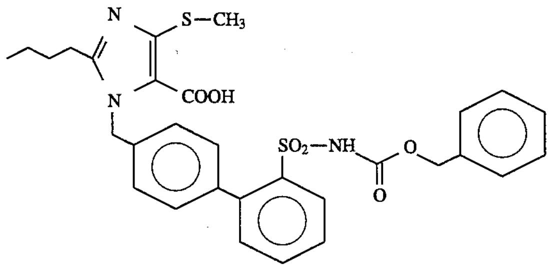

The title compound is synthesized analogously to Example 181.

$R_f$ (EA/MeOH 10:1)=0.1 MS (FAB)=594 ($M^+$+OH)

EXAMPLE 184

1-{[2'-Allylaminocarbonylaminosulfonyl)biphenyl- 4-ylmethyl}-2-n-butyl-4-methoxyimidazole-5-carbaldehyde

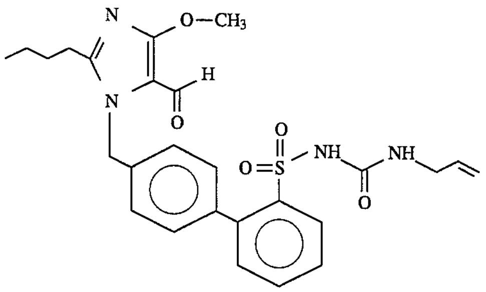

a) 1-[2'-Sulfonamidobiphenyl-4-yl)methyl]-2-n-butyl-4-methoxyimidazole-5-carbaldehyde 215 mg (0.5 mmol) of compound 1 h) and 1.5 mol of 1N NaOH are boiled under reflux in 10 ml of methanol for 19 h. The methanol is then concentrated on a rotary evaporator, and the mixture is adjusted to pH=2 using $NaHSO_4$ solution and extracted 3 times using 50 ml of EA each time. The organic phase is dried over $Na2SO_4$ and concentrated on a rotary evaporator. Chromatography using MTB/DIP (1:1) yields 170 mg (80%) of the title compound, m.p.:=189° C.

$R_f$ (MTB/DIP 1:1)=0.19 MS (DCI)=428 ($M^+$+H)

b) The title compound 184 is obtained by boiling under reflux 150 mg (0.35 mmol) of compound 184a) and 3 ml of allyl isocyanate for 5 h. The mixture is then concentrated on a rotary evaporator and chromatographed using EA. 60 mg (34%) of a colorless foam are obtained.

$R_f$ (EA)=0.34 MS (FAB)=511 ($M^+$+H)

EXAMPLE 185

1-{[(2'-Ethoxycarbonylaminosulfonyl)biphenyl-4-yl]-methyl}- 2-n-butyl-4-methoxyimidazole-5-carbaldehyde

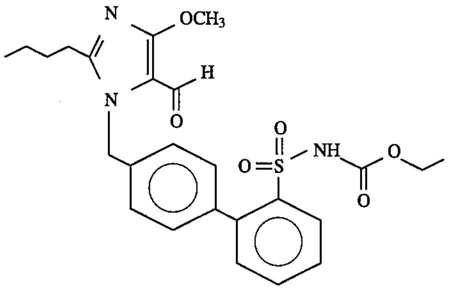

1.0 g (2.34 mmol) of compound 184a) is dissolved in 50 ml of acetone (anhydrous) and 650 mg of $K_2CO_3$ are added. The mixture is heated to reflux, then 0.45 ml of ethyl chloroformate is slowly added by syringe at this temperature. The mixture is heated under reflux for a further 4 h and then concentrated on a rotary evaporator. The residue is acidified to pH=2 using $NaHSO_4$ solution, then extracted 3 times with 100 ml of EA each time. The extract is dried over $Na_2SO_4$ and then concentrated on a rotary evaporator, and the residue is chromatographed using MTB/DIP/HOAc (15:83:2). The oil obtained can be crystallized using diethyl ether. 550 mg of colorless crystals m.p. 134° C. are obtained.

$R_f$ (MTB)=0.24 MS (FAB)=500 ($M^+$+H)

EXAMPLE 186

1-{[(2'-Benzyloxycarbonylaminosulfonyl)biphenyl- 4-]methyl}-2-n-butyl-4-methoxyimidazole-5-carbaldehyde

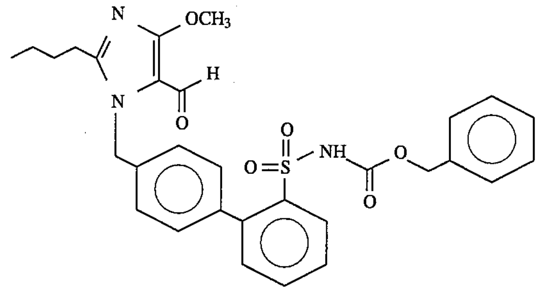

Example 186 is synthesized analogously to Example 185. $R_f$ (MTB)=0.16 MS (FAB)=562 ($M^+$+H)

EXAMPLE 187

Ethyl 1-{[(2'-benzylaminocarbonylaminosulfonyl)biphenyl-4-yl]methyl}-2-n-butylimidazole-5-carboxylate

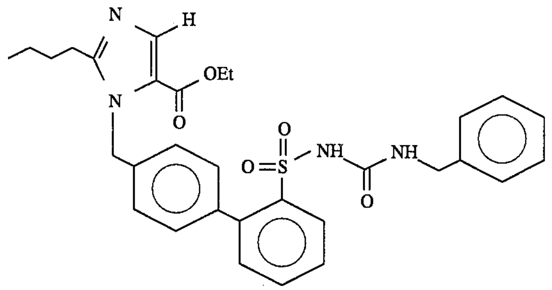

A catalytic amount of Pd/C is added to 150 mg (0.24 mmol) of compound Example 73, dissolved in 50 ml of MeOH and 5 ml of HOAc. The mixture is stirred at room temperature for 12 h in an $H_2$ atmosphere. The mixture is then concentrated on a rotary evaporator and chromatographed using EA. 30 mg (22%) of a colorless foam are obtained.

$R_f$ (EA)=0.42 MS (FAB)=575 ($M^+$+H)

EXAMPLE 188

Ethyl 1-{[(2'-ethoxycarbonylaminosulfonyl)biphenyl-4-yl]methyl}-2-n-butylimidazole-5-carboxylate

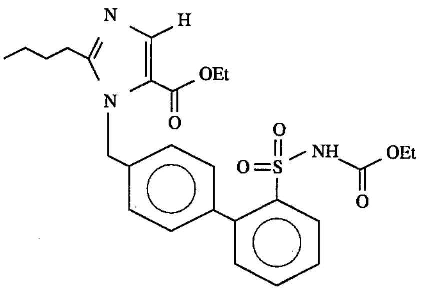

About 200 mg of Raney nickel are added to 300 mg (0.5 mmol) of compound 57 a, dissolved in 10 ml of EtOH. The mixture is heated under reflux for 10 h, a further 200 mg of Raney nickel are added and the mixture is heated under reflux for a further 5 h. The catalyst is filtered off and the solvent is concentrated on a rotary evaporator. The residue is chromatographed using MTB and 50 mg (18%) of a colorless foam are obtained.

$R_f$ (EA)=0.27 MS (FAB)=514 ($M^+$+H)

EXAMPLE 189

Ethyl 1-[(2'-{2-thienylsulfonylaminosulfonyl}biphenyl-4-yl)methyl]-2-n-butyl-4-methylthioimidazole-5-carboxylate

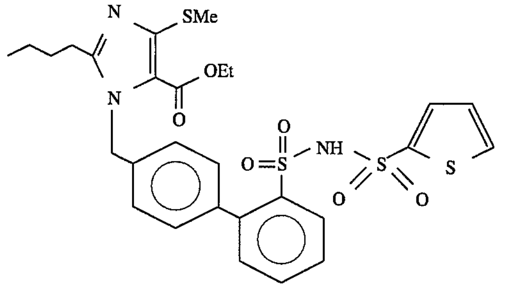

244 mg (0.5 mmol) of sulfonamide of Example 56e are dissolved in 10 ml of diethylene glycol dimethylether (anhydrous). 346 mg ( 2.5 mmol) of $K_2CO_3$ and 81 mg (0.5 mmol) of 2-thienyl sulfonyl chloride are then added. The reaction mixture is heated under reflux for 2 h, cooled and poured into 50 ml of 5% strength $NaHSO_4$ solution, and the mixture is extracted 3 times with 50 ml of EA each time. The organic phase is dried over $Na_{2so}4$, concentrated on a rotary evaporator and chromatographed using EA. 310 mg of pale yellow crystals, m.p.=120°–122° C., are obtained.

$R_f$ (EA)=0.24 MS (FAB)=634 ($M^+$+H)

EXAMPLE 190

1-[(2'-{2-Thienylsulfonylaminosulfonyl}biphenyl- 4-yl)methyl]-2-n-butyl-4-methylthioimidazole-5-carboxylic acid

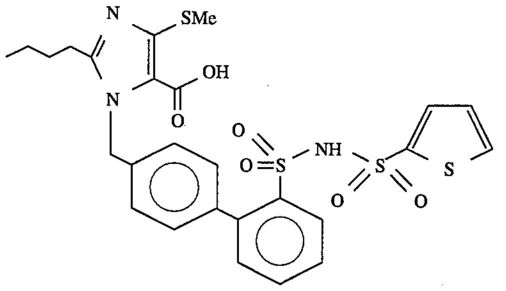

The hydrolysis of the ethyl ester from Example 189 is carried out analogously to Example 56 f $R_f$ (EA/MeOH 5:1)=0.13 MS (FAB)=606 ($M^+$+H)

The compounds of the following Table 7 can be synthesized analogously to Example 189 or analogously to Example 190 (or 56f).

These compounds have the following formula F)

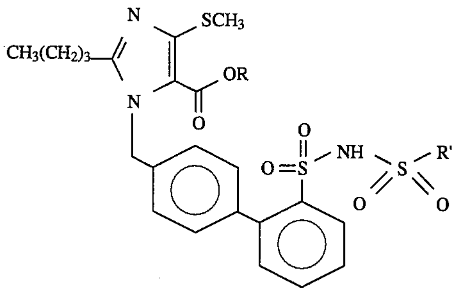

(F)

TABLE 7

| Example | MS (FAB) $M^+ + H$ | R | R' |
|---|---|---|---|
| 191 | 673 | $C_2H_5$ | 4-Nitrophenyl |
| 192 | 645 | H | " |
| 193 | 579 | $H_2H_5$ | $C_2H_5$ |
| 194 | 634 | $C_2H_5$ | 2-Thienyl |

EXAMPLE 195

Ethyl 1-[2'-methylaminocarbonylaminosulfonylbiphenyl-4-yl)methyl]-2-n-butyl-4-methylthioimidazole-5-carboxylate In an autoclave, methylamine is introduced into 1 g of sulfonylcarbamate from Example 57 a in 50 ml of toluene at 80° C. for 5 min. The mixture is then heated at 80° C. for 8 h. It is then concentrated in vacuo and the residue is chromatographed on silica gel (EA/HEP 2:1), the title compound being obtained as an amorphous powder.

$R_f$ (EA/HEP 2:1)=0.1 MS (FAB)=545 ($M^+$+H)

The compounds of the following Table 8 can be synthesized in an analogous manner to that in Example 195 or 56f (the compound from Example 195 is also listed).

These compounds have the formula C

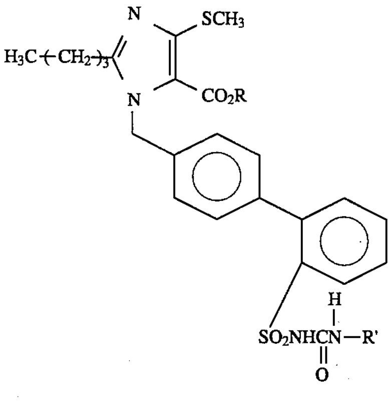

(C)

TABLE 8

| Example | MS (FAB) $M^+ + H$ | R | R' |
|---|---|---|---|
| 195 | 545 | $—C_2H_5$ | $—CH_3$ |
| 196 | 517 | H | $—CH_3$ |
| 197 | 559 | $—C_2H_5$ | $—C_2H_5$ |
| 198 | 531 | H | $—C_2H_5$ |
| 199* | 619 | $—C_2H_5$ | $—CH_2—CH_2—O—CH_2—CH_2—OH$ |

TABLE 8-continued

| Example | MS (FAB) $M^+ + H$ | R | R' |
|---|---|---|---|
| 200* | 591 | H | $—CH_2—CH_2—O—CH_2—CH_2—OH$ |

*The compounds are synthesized analogously to Example 57.

We claim:

1. A compound of the formula (I)

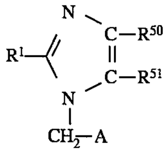

(I)

wherein the symbols have the following meanings:

$R^1$ is ($C_2$–$C_{10}$)-alkyl, ($C_3$–$C_{10}$)-alkenyl, or ($C_3$–$C_8$)-cycloalkyl;

$R^{50}$ and $R^{51}$ are each independently selected from $—S(O)_r—R^{19}$, $—CO—R^8$, and $—O—R^6$;

each $R^5$ is independently hydrogen or ($C_1$–$C_6$)-alkyl;

each $R^6$ is independently (1) hydrogen;

(2) ($C_1$–$C_6$)-alkyl, which is optionally substituted by 1 to 3 identical or different radicals selected from the group consisting of ($C_1C_6$)-alkoxy, hydroxy, carboxy, and ($C_1$–$C_4$)-alkoxycarbonyl; ($C_2$–$C_4$)-alkenyl, which is optionally substituted by phenyl; or ($C_3$–$C_6$)-alkynyl;

(3) ($C_3$–$C_8$)-cycloalkyl, ($C_3$–$C_8$)-cycloalkyl-($C_1$–$C_3$)-alkyl;

(4) ($C_6$–$C_{12}$)-aryl;

(5) ($C_6$–$C_{10}$)-aryl-($C_1$–$C_4$)-alkyl, which is optionally substituted by 1 or 2 identical or different radicals selected from the group consisting of trifluoromethyl, methoxy, halogen, and $—NR^{11}R^{12}$;

(6) ($C_1$–$C_9$)-heteroaryl, which is optionally partially or completely hydrogenated;

(7) ($C_2$–$C_{10}$)-alkenoyl;

(8) ($C_6$–$C_{12}$)-aryl or ($C_1$–$C_9$)-heteroaryl substituted by 1 or 2 identical or different radicals selected from the group consisting of halogen, hydroxy, methoxy, nitro, cyano, trifluoromethyl, $—NR^{11}R^{12}$; or (9) ($C_1$–$C_9$)-heteroaryl-($C_1$–$C_3$)-alkyl, where the heteroaryl moiety is optionally partially or completely hydrogenated;

each $R^8$ is independently hydrogen or $—OR^6$;

$R^9$ is hydrogen, ($C_1$–$C_6$)-alkyl, ($C_3$–$C_8$)-cycloalkyl or ($C_2$–$C_4$)-alkenyl;

$R^{11}$ and $R^{12}$ are, independently of one another, hydrogen or ($C_1$–$C_4$)-alkyl;

A is a biphenyl radical which is substituted by a radical $R^{15}$;

$R^{15}$ is $—SO_2—NH—CO—NR^6R^9$, $—SO_2—NH—COOR^6$, $—SO_2—NH—COR^6$, or $—SO_2—NH—SO_2—NR^6R^9$;

each $R^{19}$ is independently ($C_1$–$C_6$)-alkyl, in which one to all of the hydrogen atoms is optionally substituted by fluorine; ($C_3$–$C_8$)-cycloalkyl; phenyl; or benzyl;

r is zero, 1, or 2; and wherein ($C_1$–$C_9$)-heteroaryl and ($C_1$–$C_9$)-heteroaryl- recited above are independently selected from the group consisting of furanyl, thienyl, pyrrolyl, imidazolyl, pyrazolyl, triazolyl, tetrazolyl, oxazolyl, isoxazolyl, thiazolyl, isothiazolyl, pyridyl, pyrazinyl, pyrimidinyl, pyradazinyl, indolyl, indazolyl, quinolyl, isoquinolyl, phthalazinyl, quinoxalinyl, quinazolinyl, and cinnolinyl; or a physiologically tolerable salt thereof.

2. A compound of the formula (I)

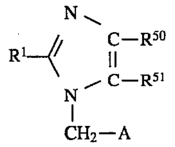

(I)

wherein the symbols have the following meanings:

$R^1$ is $(C_2-C_{10})$-alkyl, $(C_3-C_{10})$-alkenyl, or $(C_3-C_8)$-cycloalkyl;

$R^{50}$ and $R^{51}$ are each independently selected from —$S(O)_r$—$R^{19}$, —CO—$R^8$, and —O—$R^6$;

each $R^5$ is independently hydrogen or $(C_1-C_6)$-alkyl;

each $R^6$ is independently (1) hydrogen;

(2) $(C_1-C_6)$-alkyl, which is optionally substituted by 1 to 3 identical or different radicals selected from the group consisting of $(C_1-C_6)$-alkoxy, hydroxy, carboxy, and $(C_1-C_4)$-alkoxycarbonyl;
$(C_2-C_4)$-alkenyl; or
$(C_3-C_6)$-alkynyl;

(3) $(C_3-C_8)$-cycloalkyl, $(C_3-C_8)$-cycloalkyl-$(C_1-C_3$-alkyl;

(4) $(C_6-C_{12})$-aryl;

(5) $(C_6-C_{10})$-aryl-$(C_1-C_4)$-alkyl, which is optionally substituted by 1 or 2 identical or different radicals selected from the group consisting of trifluoromethyl, methoxy, halogen, and —$NR^{11}R^{12}$;

(6) $(C_2-C_{12})$-alkenoyl; or (7) $(C_6-C_{12})$-aryl substituted by 1 or 2 identical or different radicals selected from the group consisting of halogen, hydroxy, methoxy, nitro, cyano, trifluoromethyl, and —$NR^{11}R^{12}$;

each $R^8$ is independently hydrogen or —$OR^6$;

$R^9$ is hydrogen, $(C_1-C_6)$-alkyl, $(C_3-C_8)$-cycloalkyl or $(C_2-C_4)$-alkenyl;

$R^{11}$ and $R^{12}$ are, independently of one another, hydrogen or $(C_1-C_4)$-alkyl;

A is a biphenyl radical which is substituted by a radical $R^{15}$;

$R^{15}$ is —$SO_2$—NH—CO—$NR^6R^9$, —$SO_2$—NH—$COOR^6$, —$SO_2$—NH—$COR^6$, or —$SO_2$—NH—$SO_2$—$NR^6R^6$;

each $R^{19}$ is independently $(C_1-C_6)$-alkyl, in which one to all of the hydrogen atoms is optionally substituted by fluorine; $(C_3-C_8)$-cycloalkyl; phenyl; or benzyl;

r is zero, 1, or 2;

or a physiologically tolerable salt thereof.

3. A compound of claim 1 or a physiologically tolerable salt thereof, wherein:

R is $(C_2-C_{10})$-alkyl;

each $R^{50}$ and $R^{51}$ is independently —$SCH_3$ or —CO—$R^8$;

each $R^6$ is independently hydrogen or $(C_1-C_6)$-alkyl;

each $R^8$ is independently hydrogen or —$OR^6$;

$R^9$ is hydrogen, $(C_1-C_6)$-alkyl, or $(C_2-C_4)$-alkenyl;

A is a biphenyl radical which is substituted by a radical $R^{15}$; and $R^{15}$ is —$SO_2$—NH—CO—$NR^6R^9$.

4. A pharmaceutical composition comprising an effective amount of the compound of claim 1 or a physiologically tolerable salt thereof and a pharmaceutically utilizable excipient.

5. A pharmaceutical composition comprising an effective amount of the compound of claim 2 or a physiologically tolerable salt thereof and a pharmaceutically utilizable excipient.

6. A pharmaceutical composition comprising an effective amount of the compound of claim 3 or a physiologically tolerable salt thereof and a pharmaceutically utilizable excipient.

7. A method for the treatment of high blood pressure which comprises administering to a subject in recognized need of treatment for high blood pressure an effective amount of the compound of claim 1 or a physiologically tolerable salt thereof.

8. A method for the treatment of high blood pressure which comprises administering to a subject in recognized need of treatment for high blood pressure an effective amount of the compound of claim 2 or a physiologically tolerable salt thereof.

9. A method for the treatment of high blood pressure which comprises administering to a subject in recognized need of treatment for high blood pressure an effective amount of the compound of claim 3 or a physiologically tolerable salt thereof.

10. A compound of claim 1, wherein the compound is ethyl 1-[(2'-n-propyl-aminocarbonylaminosulfonylbiphenyl-4-yl)methyl]- 2-n-butyl-4-methylthioimidazol-5-carboxylate or a physiologically tolerable salt thereof.

11. A compound of claim 1, wherein the compound is 1-[( 2-'-n-propyl-aminocarbonylaminosulfonylbiphenyl-4-yl)methyl]- 2-n-butyl-4-methylthioimidazol-5-carboxylic acid or a physiologically tolerable salt thereof.

12. A pharmaceutical composition comprising an effective amount of the compound of claim 11 or a physiologically tolerable salt thereof and a pharmaceutically utilizable excipient.

13. A pharmaceutical composition comprising an effective amount of the compound of claim 10 or a physiologically tolerable salt thereof and a pharmaceutically utilizable excipient.

14. A method for the treatment of high blood pressure which comprises administering to a subject an effective amount of the compound of claim 11 or a physiologically tolerable salt thereof.

15. A method for the treatment of high blood pressure which comprises administering to a subject an effective amount of the compound of claim 10 or a physiologically tolerable salt thereof.

16. A compound of claim 1 or a physiologically tolerable salt thereof, wherein $R^{50}$ is —$S(O)_r$—$R^{19}$ or —O——$R^6$ and $R^{51}$ is —CO—$R^8$.

17. A compound of claim 1 or a physiologically tolerable salt thereof, wherein $R^{50}$ is —$S(O)_r$—$R^{19}$ and $R^{51}$ is —CO—$R^8$.

* * * * *

UNITED STATES PATENT AND TRADEMARK OFFICE

CERTIFICATE OF CORRECTION

PATENT NO. : 5,482,957

DATED : January 09, 1996

INVENTOR(S) : Adalbert WAGNER et al

It is certified that error appears in the above-indentified patent and that said Letters Patent is hereby corrected as shown below:

In Claim 1, Col. 58, line 30, "$(C_1C_6)$-alkoxy" should read --$(C_1-C_6)$-alkoxy--.

In Claim 1, Col. 58, line 46, before "$-NR^{11}R^{12}$;", insert --and--.

In Claim 2, Col. 59, lines 28-29, "$(C_3-C_8)$-cycloalkyl-$(C_1-C_3$-alkyl;" should read --$(C_3-C_8)$-cycloalkyl-$(C_1-C_3)$-alkyl;--.

In Claim 2, Col. 59, line 35, "$(C_2-C_{12})$-alkenoyl;" should read --$(C_2-C_{10})$-alkenoyl;--.

In Claim 2, Col. 59, lines 49-50, "$-SO_2-NH-SO_2-NR^6R^6$;" should read ---$SO_2-NH-SO_2-NR^6R^9$;--.

In claim 3, Col. 59, line 59, "R" should read--$R^1$--.

In claim 11, Col. 60, lines 37-38, "1-[(2-′-n-propyl-" should read --1-[(2′-n-propyl---.

UNITED STATES PATENT AND TRADEMARK OFFICE

CERTIFICATE OF CORRECTION

PATENT NO. : 5,482,957

DATED : January 09, 1996

INVENTOR(S) : Adalbert WAGNER et al

It is certified that error appears in the above-indentified patent and that said Letters Patent is hereby corrected as shown below:

In the Title, line 2, after "PREPARATION", insert --,--.

Signed and Sealed this

Third Day of December, 1996

Attest:

Bruce Lehman

BRUCE LEHMAN

Attesting Officer

Commissioner of Patents and Trademarks